(12) United States Patent
Min et al.

(10) Patent No.: US 11,730,967 B2
(45) Date of Patent: Aug. 22, 2023

(54) SYSTEMS AND METHODS FOR IMPROVED HIS BUNDLE AND BACKUP PACING TIMING

(71) Applicant: Pacesetter, Inc., Sylmar, CA (US)

(72) Inventors: Xiaoyi Min, Camarillo, CA (US); Wenwen Li, San Jose, CA (US); Yun Qiao, Sunnyvale, CA (US); Aditya Goil, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 352 days.

(21) Appl. No.: 16/904,837

(22) Filed: Jun. 18, 2020

(65) Prior Publication Data
US 2021/0393967 A1 Dec. 23, 2021

(51) Int. Cl.
*A61N 1/37* (2006.01)
*A61N 1/365* (2006.01)
*A61N 1/39* (2006.01)

(52) U.S. Cl.
CPC ......... *A61N 1/371* (2013.01); *A61N 1/36521* (2013.01); *A61N 1/36592* (2013.01); *A61N 1/3937* (2013.01); *A61N 1/39622* (2017.08)

(58) Field of Classification Search
CPC .. A61N 1/36585; A61N 1/3682; A61N 1/371; A61N 1/39622
See application file for complete search history.

(56) References Cited

U.S. PATENT DOCUMENTS

| | | | | |
|---|---|---|---|---|
| 4,878,497 A | * | 11/1989 | Callaghan | A61N 1/3706 607/30 |
| 6,212,428 B1 | * | 4/2001 | Hsu | A61N 1/3956 600/515 |
| 10,773,086 B2 | * | 9/2020 | Sheldon | A61B 5/366 |
| 11,052,255 B2 | * | 7/2021 | Brisben | A61N 1/3684 |
| 11,103,709 B2 | * | 8/2021 | Shuros | A61N 1/3712 |

(Continued)

*Primary Examiner* — Allen Porter
(74) *Attorney, Agent, or Firm* — The Small Patent Law Group LLC; Dean D. Small

(57) ABSTRACT

A system and method are provided. The system includes a HIS electrode configured to be located proximate to a HIS bundle. A pulse generator is coupled to the HIS electrode and is configured to deliver HIS bundle pacing (HBP), a right atrial (RA) electrode is located in a right atrium, a sensing circuitry coupled to the RA electrode and defines an RA sensing channel that does not utilize the HIS electrode. The system includes a memory including program instructions. The system includes a processor is configured to collect cardiac activity (CA) signals over the RA sensing channel utilizing the RA electrode. The CA signals include a far field (FF) component associated with a ventricular event (VE). The processor analyzes the FF component to identify first and second FF component (FFC) characteristics of interest (COI) of the ventricular event and utilizes the first FFC COI to apply a first capture class (CC) discriminator to distinguish between first and second capture classes. The first capture class includes first and second capture types. The processor utilizes the second FFC COI to apply a second CC discriminator to distinguish between at least one of i) the first and second capture types within the first capture class, or ii) third and fourth capture classes and manages HIS bundle pacing based on distinctions by the first and second CC discriminators.

22 Claims, 11 Drawing Sheets

(56) References Cited

U.S. PATENT DOCUMENTS

| | | | |
|---|---|---|---|
| 11,207,528 B2* | 12/2021 | Ternes | A61N 1/3702 |
| 2017/0296086 A1* | 10/2017 | Ternes | A61B 5/318 |
| 2019/0275329 A1* | 9/2019 | Brisben | A61N 1/3621 |
| 2022/0054835 A1* | 2/2022 | Doerr | A61N 1/3621 |

* cited by examiner

SYSTEMS AND METHODS FOR IMPROVED HIS BUNDLE AND BACKUP PACING TIMING

RELATED APPLICATIONS

The present application generally relates to the following co-pending applications (hereafter collectively the "Co-pending Applications"), the complete subject matter of which are expressly incorporated herein by reference in their entireties:

U.S. application Ser. No. 16/871,166, Titled "SYSTEMS AND METHODS FOR IMPROVED HIS BUNDLE AND BACKUP PACING TIMING", filed May 11, 2020;

U.S. Provisional Application 62/875,863, Titled "SYSTEMS AND METHODS FOR IMPROVED HIS BUNDLE AND BACKUP PACING TIMING", filed Jul. 18, 2019;

U.S. application Ser. No. 16/181,234, Titled "AUTOMATED OPTIMIZATION OF HIS BUNDLE PACING FOR CARDIAC RESYNCHRONIZATION THERAPY", filed Nov. 5, 2018;

U.S. application Ser. No. 16/138,766, Titled "SYSTEMS AND METHODS FOR AUTOMATED CAPTURE THRESHOLD TESTING AND ASSOCIATED HIS BUNDLE PACING", filed Sep. 21, 2018;

U.S. application Ser. No. 15/653,357, Titled "SYSTEMS AND METHODS FOR AUTOMATED CAPTURE THRESHOLD TESTING AND ASSOCIATED HIS BUNDLE PACING", filed Jul. 18, 2017; and U.S. Provisional Application 62/948,047, Titled "AUTOMATIC PACING IMPULSE CALIBRATION USING PACING RESPONSE TRANSITIONS", filed Dec. 13, 2019.

FIELD

This disclosure relates generally to implantable medical devices, and more specifically to implantable medical devices that provide HIS bundle pacing.

BACKGROUND

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (AV) node and a ventricular conduction system comprised of the bundle of HIS (also referred to as the HIS bundle), the left and right bundle branches, and the Purkinje fibers, causing a depolarization and the resulting ventricular chamber contractions.

Numerous types of therapies are utilized by implantable medical devices in connection with various heart arrhythmias. More recently, interest has grown in connection with pacing therapies that deliver pacing pulses to the HIS bundle, also referred to as HIS bundle pacing or HBP.

While HBP offers various advantages over other therapies in connection with certain types of heart disorders, an opportunity remains to improve upon existing HBP solutions. Various methods have been proposed that monitor certain features or characteristics and utilize certain algorithms for capture management in connection with HBP. Existing solutions implement sensing at the HIS pacing electrode and analyze features from the cardiac activity (CA) signals sensed over the HIS sensing channel.

However, certain types of beats introduce complexities for therapies that utilize a HIS sensing channel. For example, when a fusion beat is sensed at a HIS electrode (forming part of a HIS sensing channel), the fusion beat may create problems in connection with capture recognition. Fusion occurs when two or more wave fronts collide, causing a somewhat unique morphology. When the sensing electrode is proximate to the collision site for the two wave fronts, the morphology caused by the fusion may confuse certain HIS management algorithms. For example, a HIS electrode may sense collision (fusion) when HBP results in nonselective capture or myocardial only capture which caused local recruitment of myocardium propagation along the septum. The local myocardial propagation collides with conduction exiting the Purkinje fibers, thereby making it difficult for the system to determine what type of capture was achieved, namely selective capture, nonselective capture, loss of capture or myocardial only capture.

A need remains for improved methods and systems that manage capture during HBP even in the presence of fusion between intrinsic conduction and paced conduction.

BRIEF SUMMARY OF THE DISCLOSURE

In accordance with new and unique aspects herein, methods and systems are described that identify a type of capture that is achieved utilize a right atrial (RA) sensing channel to detect and analyze far field ventricular activity in connection with fusion beats and local phenomenon. By utilizing the RA sensing channel, embodiments herein simplify the morphology needed to be analyzed given that atrial P waves will occur in the near field and be readily and reliably detected over the RA sensing channel, without a risk of over sensing P waves. Embodiments herein may analyze the RA sensing channel to identify the type of capture it various times, such as in connection with a HBP pacing threshold search and/or beat to beat HBP capture.

In accordance with embodiments herein, a system is provided. The system includes a HIS electrode configured to be located proximate to a HIS bundle. A pulse generator is coupled to the HIS electrode and is configured to deliver HIS bundle pacing (HBP). A right atrial (RA) electrode is configured to be located in a right atrium. The system includes a sensing circuitry coupled to the RA electrode and configured to define an RA sensing channel that does not utilize the HIS electrode. The system includes a memory including program instructions. The system includes a processor, when executing the program instructions, is configured to collect cardiac activity (CA) signals over the RA sensing channel utilizing the RA electrode. The CA signals include a far field (FF) component associated with a ventricular event (VE). The processor analyzes the FF component to identify first and second FF component (FFC) characteristics of interest (COI) of the ventricular event and utilizes the first FFC COI to apply a first capture class (CC) discriminator to distinguish between first and second capture classes. The first capture class includes first and second capture types. The processor utilizes the second FFC COI to apply a second CC discriminator to distinguish between at least one of i) the first and second capture types within the first capture class, or ii) third and fourth capture classes and manages HIS bundle pacing based on distinctions by the first and second CC discriminators.

Optionally, the first FFC COI may correspond to onset of the VE. The processor may be further configured to determine an activation time between a time of a paced or intrinsic atrial event and the onset of the VE. The first FFC COI may correspond to at least one of an atria-ventricular (AV) interval to VE onset, an area of the VE, a width of the VE or a maximum slope of the VE. The processor, by utilizing the first FFC COI, may be configured to distinguish between first and second capture classes independent of whether fusion occurs between first and second wavefronts proximate the HIS electrode. The first wavefront may propagate in response to a paced event at the HIS electrode. The second wavefront may correspond to intrinsic conduction.

Optionally, the CA signals collected over the RA sensing channel avoids sensing fusion beats may represent a collision between i) a HBP causing nonselective capture or myocardial-only capture and ii) conduction exiting Purkinje fibers. The first FFC COI may corresponds to an atria-ventricular (AV) interval to VE onset and the first CC discriminator may distinguish between a first CC that may include nonselective, selective and myocardial only capture and a second CC that may include intrinsic capture and loss of capture. The second FFC COI may correspond to a width of the VE and the second CC discriminator may distinguish between the myocardial-only capture and a third capture class that may include the nonselective and selective capture.

Optionally, the second FFC COI may correspond to at least one of an area of the VE or a width of the VE and the second CC discriminator may distinguish between the third and fourth capture classes. The third capture class may include selective and nonselective capture. The fourth capture class may include at least myocardial-only capture. The first FFC COI may correspond to an area of the VE and the first CC discriminator may distinguish between i) myocardial-only capture, ii) nonselective capture, and iii) the first capture class that may include selective capture, intrinsic capture and loss of capture. The second FFC COI may correspond to an atria-ventricular (AV) interval to VE onset and the second CC discriminator may distinguish between the selective capture and a third capture class that may include the loss of capture and intrinsic capture.

Optionally, the processor may be configured to overlay a search window on the CA signals collected over the RA sensing channel. The search window may be positioned to follow a paced or sensed atrial event by a predetermined amount of time to align the search window with a period of time during which the VE is expected to occur. The processor may be further configured to identify a peak in the CA signals and to separately perform forward and backward searches along the CA signals from the peak to identify an onset intercept and a termination intercept of the VE. The processor may be further configured to identify a largest peak and a largest valley in a search window and to reset intercept points separately for the forward and backward searches from the largest peak and separately for the forward and backward searches from the largest valley.

In accordance with embodiments herein, a computer implemented method is provided. The method utilizes a processor configured to execute program instructions to perform. The method delivers HIS bundle pacing (HBP) and collects cardiac activity (CA) signals over a right atrial (RA) sensing channel utilizing an RA electrode. The CA signals include a far field (FF) component associated with a ventricular event (VE). The method analyzes the FF component to identify first and second FF component (FFC) characteristics of interest (COI) of the ventricular event. The method first distinguishes between first and second capture classes (CCs) based on the first FFC COI. The first capture class includes first and second capture types. The method second distinguishes between at least one of i) the first and second capture types within the first capture class, or ii) third and fourth capture classes based on the second FFC COI. The method manages HIS bundle pacing based on the first and second distinguishing operations.

Optionally, the first FFC COI may correspond to onset of the VE. The method may further comprises determining an activation time between a time of a paced or intrinsic atrial event and onset of the VE. The first FFC COI may correspond to at least one of an atria-ventricular (AV) interval to VE onset, an area of the VE, a width of the VE or a maximum slope of the VE. The first distinguishing between first and second capture classes may be independent of whether fusion occurs between first and second wavefronts proximate a HIS electrode. The first wavefront may propagate in response to a paced event at the HIS electrode. The second wavefront may correspond to intrinsic conduction. The method may comprise, during collection of the CA signals over the RA sensing channel, may avoid sensing fusion beats representing a collision between i) a HBP causing nonselective capture or myocardial-only capture and ii) conduction exiting Purkinje fibers.

Optionally, the first FFC COI may correspond to an atria-ventricular (AV) interval to VE onset and the first distinguishing may distinguish between a first CC that includes nonselective, selective and myocardial-only capture and a second CC that may include intrinsic capture and loss of capture. The second FFC COI may correspond to a width of the VE and the second distinguishing may distinguish between the myocardial-only capture and a third capture class that may include the nonselective and selective capture. The second FFC COI may corresponds to at least one of an area of the VE or a width of the VE and the second distinguishing may distinguish between the third and fourth capture classes. The third capture class may include selective and nonselective capture. The fourth capture class may include at least myocardial-only capture.

Optionally, the first FFC COI may correspond to an area of the VE and the first distinguishing may distinguish between i) myocardial-only capture, ii) nonselective capture, and iii) the first capture class that includes selective capture, intrinsic capture and loss of capture. The second FFC COI may correspond to an atria-ventricular (AV) interval to VE onset and the second distinguishing may distinguish between i) the selective capture and a third capture class that includes the loss of capture and intrinsic capture.

BRIEF DESCRIPTION OF THE DRAWINGS

The various features of the present disclosure and the manner of attaining them will be described in greater detail with reference to the following description, claims, and drawings.

DETAILED DESCRIPTION

Figure 1:
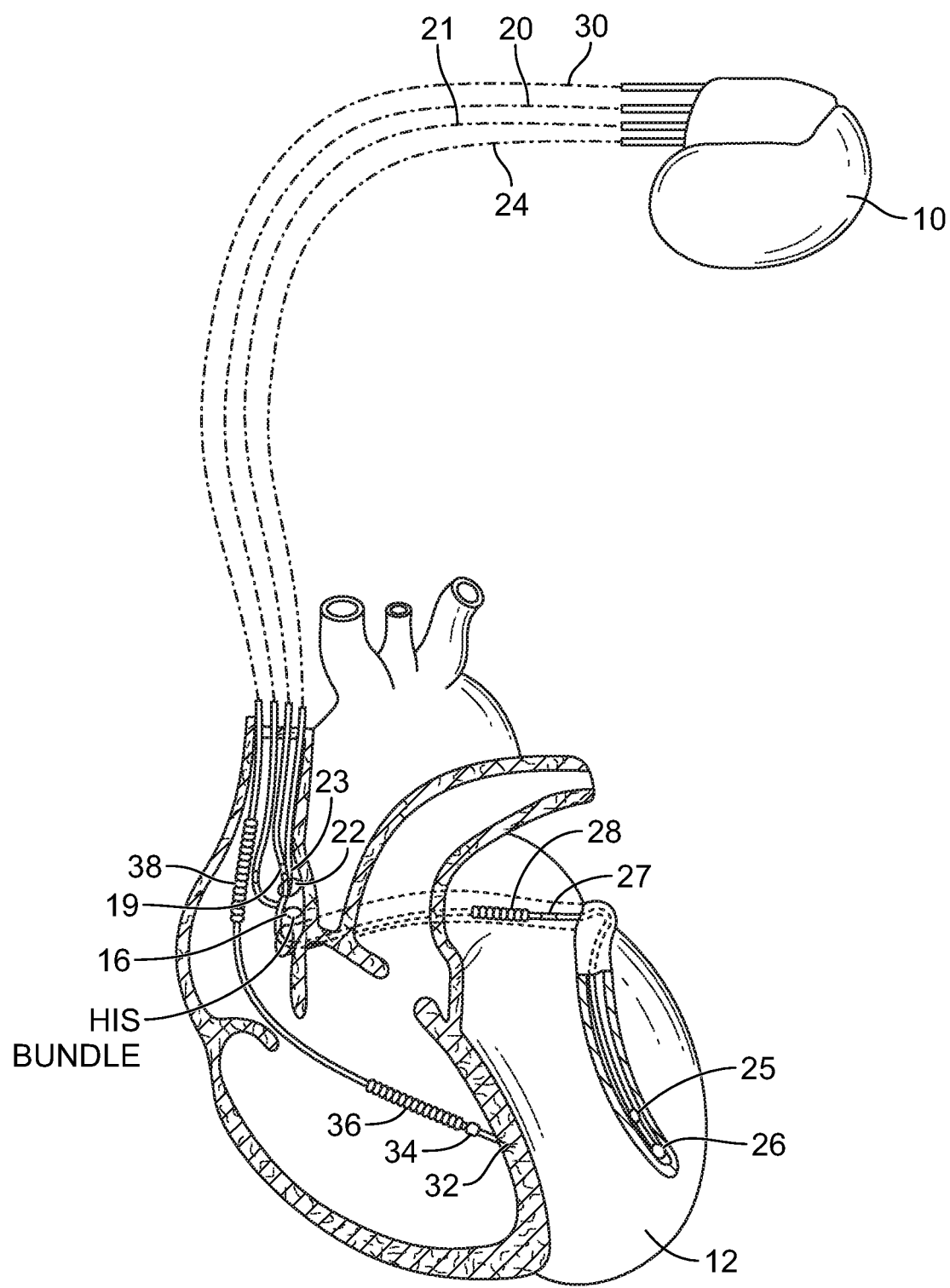
FIG. 1 illustrates an implantable stimulation device in electrical communication with at least four leads, including a HIS Bundle lead, implanted into a patient's heart for delivering multi-chamber stimulation and shock therapy.

The present disclosure is directed to various aspects of stimulation devices and corresponding methods related to HIS bundle pacing. Among other things, the present disclosure provides methods and devices for automatic determination of HIS bundle capture thresholds, for configuring stimulation devices based on determined capture thresholds, for identifying different capture types in response to application of pacing impulses, and other related features and functions. Aspects of the present disclosure may be implemented in either a dual chamber or multi-chamber cardiac stimulation device.

Certain cardiac pacemakers and defibrillators incorporate a pacing lead in the right ventricle and may also include a second lead in the right atrium. High-burden right ventricle pacing may contribute to the development of pacing-induced cardiomyopathy and symptoms associated with heart failure (HF). Several pathophysiologic mechanisms have been implicated in the development of pacing-induced HF, each of which likely stems from non-physiological electrical and mechanical activation patterns produced by right ventricle pacing. HIS bundle pacing (HBP) may restore physiological activation patterns by utilizing a patient's intrinsic conduction system and may do so even in the presence of bundle branch block. HBP has also been shown to provide significant QRS narrowing, with improved ejection fraction.

Another possible clinical application of HBP is cardiac resynchronization therapy (CRT). Conventional CRT systems include pacing from both a right ventricular and a left ventricular lead and have been shown most effective for patients exhibiting a wide QRS complex and left bundle branch block. HBP has also been shown to be effective at narrowing the QRS complex in patients with left bundle branch block, likely due to restoration of conduction through HIS and Purkinje, which includes right and left bundle fibers that are longitudinally dissociated. Therefore, what is thought of as left bundle branch block, can be a result of a proximal blockage within the HIS bundle that eventually branches to the left bundle. As a result, by pacing the HIS bundle distal to the blockage, a normalized QRS complex can be achieved in some patients. Theoretically, this pacing mode may provide even better results than known CRT treatments, as activation propagates rapidly through natural conduction pathways.

The HIS bundle is a narrow cluster of cardiac muscle fibers that passes electrical impulses from the AV node to the interventricular septum. It is anatomically located adjacent to the annulus of the tricuspid valve, inferior to or within the membranous septum. During normal functioning of the heart, the delay between excitation of the HIS bundle and a subsequent depolarization of the ventricles in response to the excitation is generally on the order of approximately 30-50 milliseconds (ms) and the resulting QRS complex generally has a duration of approximately 70-100 ms.

Depending on electrode position, pacing leads targeted for the HIS bundle may achieve either non-selective or selective HBP. Non-selective HIS bundle pacing (nsHBP) refers to pacing of the HIS bundle in which both the HIS bundle and the local myocardium surrounding the HIS bundle are captured. Capture occurs when an electrical stimulus applied to the heart is of sufficient energy to depolarize the cardiac tissue near stimulation electrodes and propagate, thereby causing the heart muscle to contract. As a result of the simultaneous depolarization of multiple areas of cardiac tissue, the sequential electrical responses typically observed during normal heart activity may be combined or condensed. HIS bundle capture resulting in such a response is often characterized by the stimulus to ventricular depolarization duration being short, on the order of 20 ms, because the myocardial depolarization propagates immediately without exclusively traveling through the His-Purkinje system. Because the HIS bundle is stimulated and captured, the QRS duration is similar to the native QRS duration but may be slightly longer due to the myocardial excitation (e.g., 70-120 ms). In contrast, selective HIS bundle pacing (sHBP) refers to exclusive capture of the HIS bundle without stimulating surrounding myocardial tissue. With sHBP, the stimulus to ventricular depolarization interval is virtually the same as the native delay between HIS bundle stimulation and subsequent ventricular depolarization and the QRS duration is essentially identical to the native QRS duration.

Embodiments may be implemented in connection with one or more or more of the Co-pending Applications.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference.

Additionally or alternatively, embodiments may be implemented in connection with one or more combination of leadless implantable medical devices (LIMD) that communicate with one another and include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference. For example, a first LIMD may be implanted in RA and a second LIMD may be implanted in the HIS, where the first and second LIMDs communicate with one another to coordinate operation therebetween.

Additionally or alternatively, the IMD may be implemented in combination with a subcutaneous IMD that includes one or more structural and/or functional aspects of the device(s) described in U.S. application Ser. No. 15/973, 195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

Additionally or alternatively, the IMD may be implemented in combination one or more leadless cardiac monitor (ICM) that includes one or more structural and/or functional aspects of the device(s) described in U.S. patent application , U.S. patent application Ser. No. 15/084,373, filed Mar. 29, 2016, entitled, "METHOD AND SYSTEM TO DISCRIMINATE RHYTHM PATTERNS IN CARDIAC ACTIVITY," which is expressly incorporated herein by reference.

All references, including publications, patent applications and patents, cited herein are hereby incorporated by reference to the same extent as if each reference were individually and specifically indicated to be incorporated by reference and were set forth in its entirety herein.

Overview of HBP System and Components

During HIS bundle pacing (HBP), a stimulus is applied at a predetermined time ($t_s$) following an atrial event. The stimulus may result in various types of capture, such as selective HIS bundle capture (sHBP), nonselective HIS bundle capture (nsHBP), myocardium only capture (myo-only) or no capture referred to as loss of capture (LOC). When selective HIS bundle capture occurs, only the HIS bundle is captured and the myocardium is not excited by the stimulus applied at the HIS bundle. As a result, while the delay between application of the stimulus and onset of the QRS complex may vary for a given patient, it is generally in the range of approximately 30 to 50 ms, which is generally consistent with normal heart function. The resulting QRS may be narrowed but is typically between 70 and 100 ms in duration. In contrast, when non-selective HIS bundle capture occurs both the HIS bundle and the myocardium are captured. With non-selective capture the delay between application of the stimulus and the onset of the QRS complex is reduced (typically less than 10 ms) and the QRS duration generally remains between 70 and 120 ms. Non-selective HIS bundle capture may also result in the occurrence of a delta wave, which is generally a slurred upstroke in the QRS complex resulting from local excitation of the ventricles near a HIS lead.

Because sHBP more closely approximates native heart function, it is generally preferred to nsHBP. However, due to the complexity and dynamic nature of certain cardiomyopathies and cardiac anatomies, sHBP may not be possible or, if possible at one time, may no longer be possible as a patient's condition changes. Moreover, a patient's condition may also change to the point where HBP is generally unsuitable as a pacing method and ventricular pacing is required.

In light of the foregoing, it is desirable to provide methods and apparatuses directed to optimizing or otherwise manage HBP of a patient's heart. To manage HBP, the stimulation device initialized and managed to dynamically modify settings to provide HBP, including to identify and dynamically modify one or more capture thresholds associated with HBP. The HBP capture threshold may vary over time for a patient and will vary within a patient population. Accordingly, HBP capture testing is performed to determine what type of capture is achieved by an HBP event delivered at a particular energy level and with a particular timing relative to intrinsic or paced atrial events. It is important to correctly identify the capture type that is achieved with a particular HBP setting (energy and timing).

Embodiments herein describe various manners to analyze cardiac activity signals collected along various sensing channels in order to identify a capture class and ultimately an individual capture type.

FIG. 1 illustrates an implantable medical device (IMD) 10 that is in electrical communication with a patient's heart 12 by way of four leads, 20, 21, 24, and 30 and suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage or atrial septum.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode within the coronary veins overlying the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus which overlies the left ventricle.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. In another embodiment, an additional electrode for providing left ventricular defibrillation shocking therapy may be included in the portion of the lead overlying the left ventricle, adjacent to the ring electrode 25.

The stimulation device 10 illustrated in FIG. 1 is generally configured as an implantable cardioverter-defibrillator (ICD) and generally includes functionality for pacing, sensing, and providing defibrillation to a patient heart. It should be appreciated however, that the ICD illustrated in FIG. 1 is just one example stimulation device that may implement aspects of the present disclosure. Other configurations and types of implantable stimulation devices incorporating aspects of the present disclosure are also contemplated. For example and without limitation, in at least one implementation, the stimulation device 10 of FIG. 1 may instead be configured as a pacemaker without defibrillation functionality and, in particular, a pacemaker configured to provide cardiac resynchronization therapy (CRT). In such implementations, some or all of the defibrillation coils illustrated on the various leads of FIG. 1 and their associated circuitry within the stimulation device 10 may be omitted. It should also be appreciated that the specific configuration of leads and placement of leads illustrated in FIG. 1 is intended merely as an example and other configurations are possible. For example, in one specific implementation, the coronary sinus lead 24 may instead be replaced with a left ventricle lead that extends and is implanted within the left ventricle for pacing and/or sensing of the left ventricle. More generally, implementations of the present disclosure are generally applicable to any suitable stimulation devices currently known or later developed that provide HIS bundle pacing.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular coil electrode 36, and a superior vena cava (SVC) coil electrode 38. Typically, the right ventricular lead 30 is transvenously inserted into the heart 12 so as to place the right ventricular tip electrode 32 in the right ventricular apex so that the right ventricular coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

The stimulation device 10 is further connected to a HIS bundle lead 21 having a HIS tip electrode 16, such as a helical active fixation device, and a HIS ring electrode 19 located proximal from the HIS tip electrode 16. In certain implementations, the HIS ring electrode 19 is located approximately 10 mm proximal the HIS tip electrode 16. The HIS bundle lead 21 may be transvenously inserted into the heart 12 so that the HIS tip electrode 16 is positioned in the tissue of the HIS bundle. Accordingly, the HIS bundle lead 21 is capable of receiving depolarization signals propagated in the HIS bundle and exiting the Purkinje fibers to the myocardium or delivering stimulation to the HIS bundle, creating a depolarization that can be propagated through the lower conductive pathways of the right and left ventricles (i.e., the right and left bundle branches and Purkinje fibers).

Figure 2:
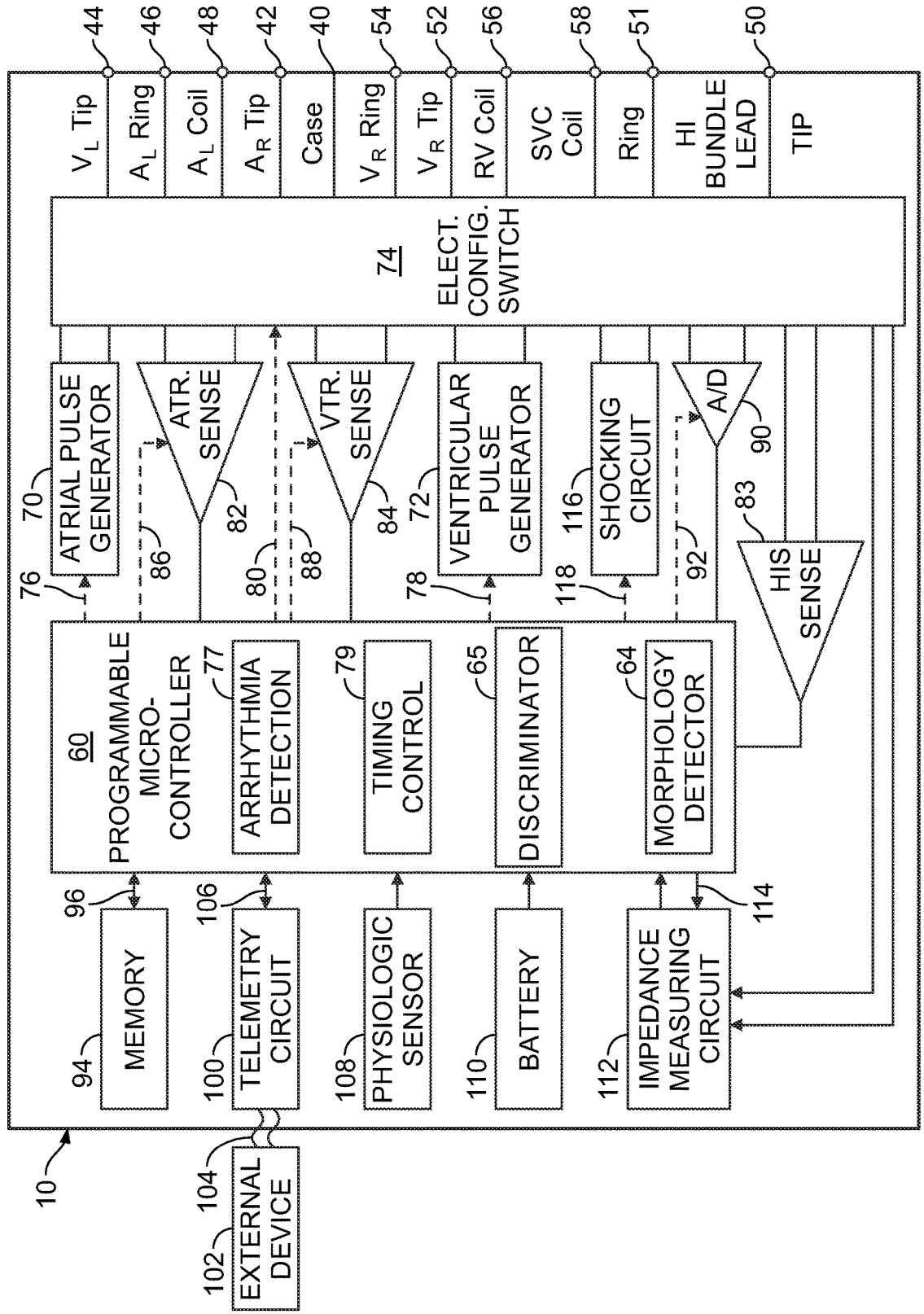
FIG. 2 illustrates a block diagram of the implantable medical device (IMD) implemented in accordance with embodiments herein.

FIG. 2 illustrates a block diagram of the implantable medical device (IMD) of FIG. 1, implemented in accordance with embodiments herein. The IMD is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10 is often referred to as the "can", "case" or "case electrode" and may be programmably selected to act as the return electrode for all "unipolar" modes. The housing 40 may further be used as a return electrode alone or in combination with one or more of the coil electrodes 28, 36, and 38 (shown in FIG. 1) for shocking purposes. The housing 40 further includes a connector (not shown) having a plurality of terminals 42, 44, 46, 48, 50-52, 54, 56, and 58 (shown schematically and, for convenience, next to the names of the electrodes to which they are connected). As such, to achieve right atrial sensing and pacing, the connector includes at least a right atrial tip terminal (AR TIP) 42 adapted for connection to the atrial tip electrode 22 (shown in FIG. 2).

To achieve left chamber sensing, pacing, and defibrillation (in applications in which the stimulation device 10 is an ICD), the connector includes at least a left ventricular tip terminal (VL TIP) 44, a left atrial ring terminal (AL RING) 46, and a left atrial shocking terminal (AL COIL) 48, which are adapted for connection to the left ventricular tip electrode 26, the left atrial ring electrode 27, and the left atrial coil electrode 28, respectively (each shown in FIG. 1).

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricular ring electrode 34, the right ventricular coil electrode 36, and the SVC coil electrode 38, respectively (each shown in FIG. 1).

To achieve HIS bundle sensing, or sensing and stimulation, the connector further includes a HIS bundle lead tip terminal 50 and a HIS bundle lead ring terminal 51 which are adapted for connection to the HIS tip electrode 16 and the HIS ring electrode 19, respectively (each shown in FIG. 1).

At the core of the stimulation device 10 is a programmable microcontroller 60 which controls the various modes of stimulation therapy. The microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present disclosure. Rather, any suitable microcontroller 60 may be used that carries out the functions described herein.

An atrial pulse generator 70 and a ventricular pulse generator 72 generate pacing stimulation pulses for delivery by the right atrial lead 20, the right ventricular lead 30, the coronary sinus lead 24, and/or the HIS bundle lead 21 via an electrode configuration switch 74. As previously noted, in certain applications, the coronary sinus lead 24 may instead be substituted with a left ventricle lead. It is understood that in order to provide stimulation therapy in each of the chambers of the heart, the atrial and ventricular pulse generators 70, 72 may include dedicated, independent pulse generators, multiplexed pulse generators, or shared pulse generators. The pulse generators 70, 72 are controlled by the microcontroller 60 via appropriate control signals 76, 78, respectively, to trigger or inhibit the stimulation pulses. As used herein, the shape of the stimulation pulses is not limited to an exact square or rectangular shape, but may assume any one of a plurality of shapes which is adequate for the delivery of an energy pulse, packet, or stimulus.

The microcontroller 60 further includes timing control circuitry 79 which is used to control the timing of such stimulation pulses (e.g., pacing rate) as well as to keep track of the timing of refractory periods, blanking intervals, noise detection windows, evoked response windows, alert intervals, marker channel timing, etc.

According to one embodiment of the present disclosure, timing control circuitry 79 also controls the onset and duration of a far field (FF) search window that is overlaid onto the CA signals sensed over the RA sensing channel. Timing control circuitry 79 also is used to mark and determine a timing of features in connection with determining a FF component (FFC) characteristic of interest (COI). For example, the timing control circuitry 79 is utilized to determine an AV interval between an AP or AS event and a VE feature of interest, such as VE onset, QRS complex termination and the like (e.g., AV interval from the A event to onset of the VE, the HV interval from the HP event to onset of the VE, the AV interval from the A event to the end of the QRS complex, the HV interval from the HP event to the end of the QRS complex and the like).

The microcontroller 60 includes a morphology detector 64 that is configured to, among other things, analyze the FF component to identify first and second FF component (FFC) characteristics of interest (COI) of the ventricular event.

The microcontroller 60 includes a discriminator 65 configured to distinguish between capture classes. For example, the discriminator may include a first capture class (CC) discriminator that applies a first FFC COI to distinguish between first and second capture classes, wherein the first capture class includes first and second capture types. The discriminator 65 includes a second CC discriminator that applies a second FFC COI to distinguish between at least one of i) the first and second capture types within the first capture class, or ii) third and fourth capture classes. The microcontroller 60 manages HIS bundle pacing based on the distinctions by the first and second CC discriminators.

For example, the first FFC COI corresponds to onset of the VE and the timing control circuit 79 is further configured to determine the activation time between the time of a paced or intrinsic A event and the onset of the VE. Additionally or alternatively, the first FFC COI corresponds to at least one of a width of the FFC, a maximum slope of the FFC or an area under a curve of the FFC. Additionally or alternatively, the discriminator 65 utilizes the first FFC COI to distinguish between first and second capture classes independent of whether fusion occurs between first and second wavefronts proximate the his electrode, the first wavefront propagating in response to a paced event at the his electrode, the second wavefront corresponding to intrinsic conduction.

The RA sensing channel avoids sensing fusion beats representing a collision between i) a HBP causing nonselective capture or myocardial only capture and ii) conduction exiting Purkinje fibers.

Additionally or alternatively, the first FFC COI corresponds to an AV interval to VE onset and the discriminator 65 distinguishes between a first CC that includes nonselective, selective and myocardial-only capture and a second CC that includes intrinsic and loss of capture. Additionally or alternatively, the second FFC COI corresponds to an width of the VE and the discriminator 65 distinguishes between the myocardial-only capture and a third capture class that includes the nonselective and selective capture. Additionally or alternatively, the second FFC COI corresponds to at least one of an area of the VE or an width of the VE and the discriminator 65 distinguishes between the third and fourth capture classes, the third capture class including selective and nonselective capture, the fourth capture class including at least myocardial-only capture. Additionally or alternatively, the first FFC COI corresponds to an area of the VE and the first CC discriminator distinguishes between i) myocardial-only capture, ii) nonselective capture, and iii) the first capture class that includes selective capture, intrinsic and loss of capture. Additionally or alternatively, the second FFC COI corresponds to an AV interval to VE onset and the discriminator 65 distinguishes between i) the selective capture and a third capture class that includes the loss of capture and intrinsic. Additionally or alternatively, the microcontroller 60 is configured to overlay a search window on the CA signals collected over the RA sensing channel, the search window positioned to follow a paced or sensed atrial event by a predetermined amount of time to align the search window with a period of time during which the VE is expected to occur. Additionally or alternatively, the microcontroller is further configured to identify a peak in the CA signals and to separately perform forward and backward searches along the CA signals from the peak to identify an onset intercept and a termination intercept of the VE. Additionally or alternatively, the microcontroller 60 is further configured to identify a largest peak and a largest valley in a search window and to reset intercept points separately for the forward and backward searches from the largest peak and separately for the forward and backward searches from the largest valley.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24 (or left ventricle lead), and the right ventricular lead 30, through the switch 74 for detecting the presence of cardiac activity in each of the four chambers of the heart. Accordingly, the atrial (ATR. SENSE) and ventricular (VTR. SENSE) sensing circuits 82, 84 may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

According to one implementation of the present disclosure, the atrial sensing circuit 82 is selectively coupled to an electrode in the RA to define a sensing channel between the RA electrode and a CAN electrode. The atrial sensing circuit 82 may define an RA sensing channel that utilizes unipolar or bipolar sensing and that generates a wideband or narrow band CA signal.

The HIS sensing circuit 83 is selectively coupled to the HIS bundle lead 21 for detecting the presence of a conducted depolarization arising in the atria and conducted through the HIS bundle via the AV node. As used herein, each of the atrial sensing circuit 82, the ventricular sensing circuit 84, and the HIS sensing circuit 83, includes a discriminator, which is a circuit that senses and can indicate or discriminate the origin of a cardiac signal in each of the cardiac chambers.

The RA and HIS sensing circuit 82, 83 are shown as dedicated circuits within the stimulation device 10. However, it should be appreciated that in certain implementations, His-related functionality may instead be provided by repurposing other pacing and sensing channels and circuitry of the stimulation device 10. For example, the stimulation device 10 may be reprogrammed such that a pacing channel, a sensing channel, and associated circuitry initially programmed for use in sensing and pacing one of the atria or ventricles may instead be reconfigured to pace and sense the HIS bundle.

Each sensing circuit 82-84 preferably employs one or more low power, precision amplifiers with programmable gain and/or automatic gain control, bandpass filtering, and a threshold detection circuit to selectively sense the cardiac signal of interest. The automatic gain control enables the device 10 to deal effectively with the difficult problem of sensing the low amplitude signal characteristics of atrial or ventricular fibrillation.

The outputs of the sensing circuits 82-84 are connected to the microcontroller 60 which, in turn, is able to trigger or inhibit the atrial and ventricular pulse generators 70, 72, respectively, in a demand fashion in response to the absence or presence of cardiac activity in the appropriate chambers of the heart.

The atrial and ventricular sensing circuits 82, 84, in turn, receive control signals over signal lines 86, 88, from the microcontroller 60 for purposes of controlling the gain, threshold, polarization charge removal circuitry (not shown), and the timing of any blocking circuitry (not shown) coupled to the inputs of the sensing circuits 82, 84.

For arrhythmia detection, the stimulation device 10 includes an arrhythmia detector 77 that utilizes the atrial and ventricular sensing circuits 82, 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (ND) data acquisition system 90 represented by an A/D converter. The data acquisition system 90 may be coupled to the microcontroller 60, or other detection circuitry, for detecting an evoked response from the heart 12 in response to an applied stimulus, thereby aiding in the detection of capture.

The microcontroller 60 performs capture detection and identification of a type of capture in accordance with the methods and systems described in the Co-pending Applications. The microcontroller 60 may utilize backup pacing in connection with capture detection and management in accordance with the methods and systems described in the Co-pending Applications. Capture detection may occur on a beat-by-beat basis or on a sampled basis. Preferably, a capture threshold search is performed at least once a day during at least the acute phase (e.g., the first 30 days following device implant) and less frequently thereafter. A capture threshold search would begin at a desired starting point for delivery of HBP (either a high energy level or the level at which capture is currently occurring) and decrease the energy level of each HIS paced event until capture is lost and/or a desired type of capture is no longer achieved (e.g., nonselective capture may still be achieved, but selective capture may no longer be achieved). The minimum energy at which capture (or a desired type of capture) is consistently obtained is known as the capture threshold. Thereafter, a safety margin can be automatically or programmably added to the capture threshold.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, FFC COI, HIS capture energy level, HIS capture AH delay, and the amplitude, waveshape and vector of each shocking pulse to be delivered to the patient's heart 12 within HBP and each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In certain implementations, the stimulation device 10 may further include a physiologic sensor 108, commonly referred to as a "rate-responsive" sensor to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, stimulation delays, etc.) at which the atrial and ventricular pulse generators 70, 72 generate stimulation pulses.

The stimulation device 10 additionally includes a battery 110 which provides operating power to all of the circuits. The device 10 includes an impedance measuring circuit 112 which is enabled by the microcontroller 60 via a control signal 114. According to one implementation of the present disclosure, the HIS tip electrode 16 and HIS ring electrode 19 may be selectively coupled via switch 74 to the impedance measuring circuit 112 for performing a tissue impedance measurement. The tissue impedance measurement may be made to determine the location of the HIS bundle as the HIS tip electrode 16, mapping collar, or sensing electrodes are advanced along the endocardial surface of the right atrium.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118.

At the distal end of the lead 21 is the HIS bundle tip electrode. The HIS bundle tip electrode is, or includes, an active fixation device, such as a helical, "screw-in," device that allows stable fixation of the electrode in the HIS bundle tissue. The distal end of the HIS bundle lead 21 is further provided with a non-traumatic conductive surface (also referred to herein interchangeably as a mapping collar). The non-traumatic conductive surface is advantageously used to make electrical measurements that indicate the location of the HIS bundle without having to anchor the HIS bundle tip electrode 16 into the endocardial tissue. The non-traumatic conductive surface and the HIS bundle tip electrode 16 are electrically coupled within the lead body of the HIS bundle lead 21 and together form one conductive element for the purposes of sensing, stimulation, and impedance measurements.

The HIS bundle lead 21 is also provided with a HIS ring electrode 19. The HIS ring electrode 19 is preferably spaced between approximately 2 mm and 30 mm, but preferably 10 mm, from the HIS tip electrode 16. The HIS ring electrode 19 may function as the return electrode during bipolar sensing, stimulation or impedance measurement operations.

The HIS tip electrode 16 and the HIS ring electrode 19 are each connected to flexible conductors 64, 66, respectively, which may run the entire length of the HIS bundle lead 21. The flexible conductor is connected to the HIS tip electrode 16 and is electrically insulated from the flexible conductor 66 by a layer of insulation. The conductor 66 is connected to the HIS ring electrode 19. The flexible conductors 64, 66 serve to electrically couple the HIS ring electrode 19 and the HIS tip electrode 16 to the HIS ring electrode terminal 51 and the HIS tip electrode terminal 50, respectively. One embodiment of the HIS bundle lead 21 is available from St. Jude Medical CRMD as lead model No. 2088T.

For more details regarding a heart electrode equipped with multiple conductive surfaces, reference is made to U.S. Pat. Nos. 5,306,292 and 5,645,580, which are incorporated herein by reference.

During the implantation procedure, the HIS bundle lead 21 is introduced transvenously into the right atrium or below the valve inside RV. It is then gradually advanced with the HIS tip electrode 16 in contact with the endocardial tissue. Electrical measurements may be made continuously as the HIS tip electrode 16 is advanced to determine the location of the HIS bundle. The non-traumatic conductive surface (helix not extended) advantageously provides electrical contact with the endocardial tissue thereby allowing electrical measurements to be performed without having to fix the HIS tip electrode 16 into the endocardial tissue using the HIS bundle tip electrode 16. RA channel based HBP capture management In accordance with new and unique aspects herein, it has been found that a far field (FF) component associated with ventricular events (VE) can be analyzed from CA signals that are collected over an RA sensing channel utilizing one or more RA electrodes that are spaced apart from the HIS electrode(s). Various characteristics of interest can be identified from the FF component of the CA signals, such as the delay from a paced or sensed atrial event to onset of a ventricular event, the width of the ventricular event, the maximum slope within the FF component associated with the VE, the area under the curve within the FF component and the like. Clinical data and literature has shown that outcomes from nonselective and selective capture may be clinically equivalent.

Figure 3A:
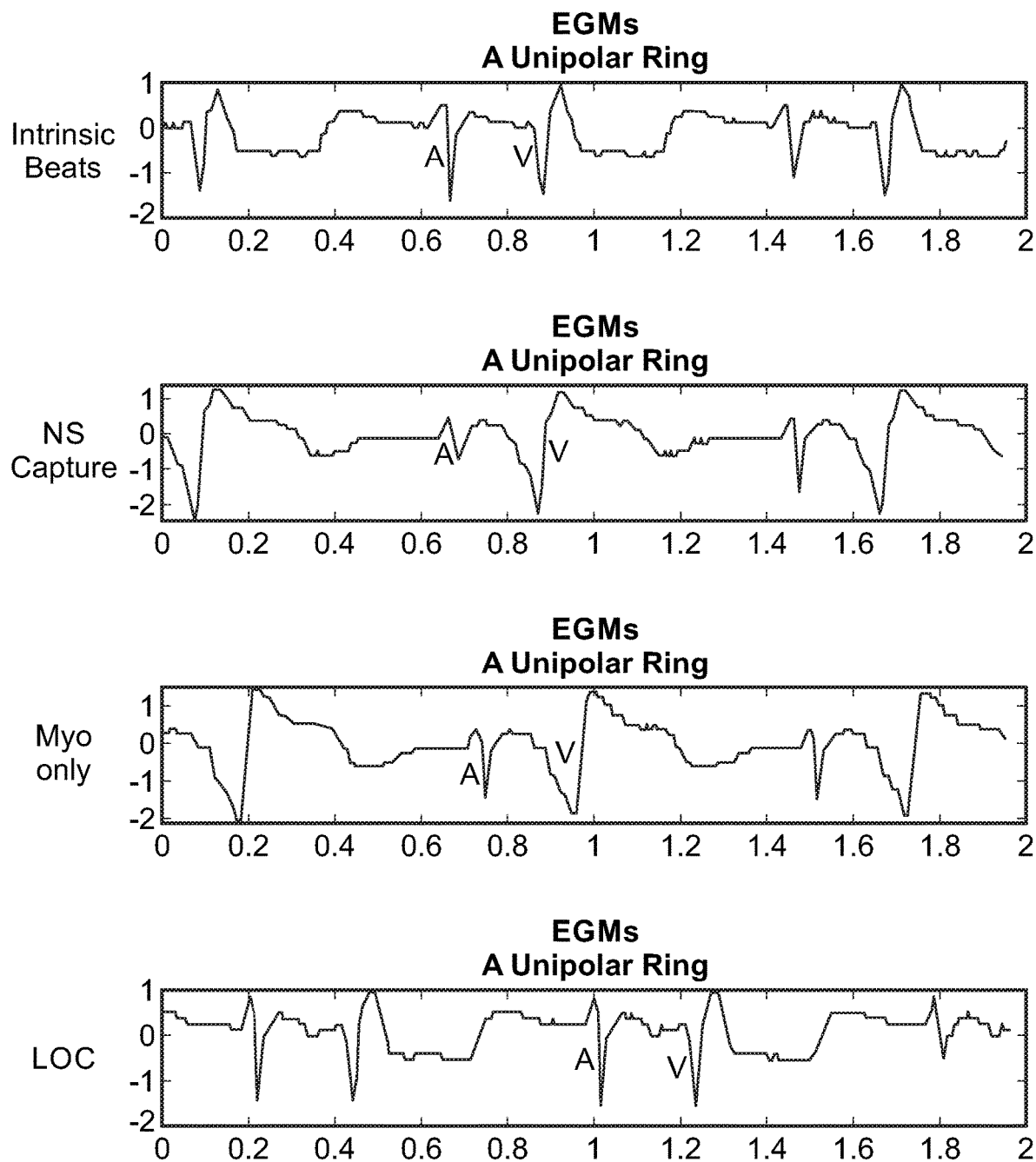
FIG. 3A illustrates examples of cardiac activity signals collected over an RA sensing channel in connection with HBP achieving different types of HBP capture.

FIG. 3A illustrates examples of cardiac activity signals collected over an RA sensing channel in connection with HBP achieving different types of HBP capture. The RA sensing channel utilized a unipolar ring electrode located in the right atrium. The RA sensing vector is defined between the ring electrode and the CAN electrode of the IMD. An atrial (A) event marker "A" and a ventricular (V) event "V" is noted on each of the I EGM signals. The cardiac activity signals represent IEGM signals collected over approximately 2s. The top panel corresponds to intrinsic heartbeats. The second from top panel corresponds to a beat in which HBP is delivered, but does not achieve any capture, namely loss of capture. The second from the bottom panel corresponds to a beat in which HBP is delivered and achieves nonselective capture. The bottom panel corresponds to a beat in which HBP is delivered and achieves selective capture.

Each of the panels illustrate the ventricular event from the far field. The far field component of each signal is well-defined and very readily apparent. In the intrinsic beat, myocardial only beat and loss of capture beat, the A event and the V event have similar magnitudes. In connection with the nonselective capture beat, the V event induces a larger signal then the A event.

Figure 3B:
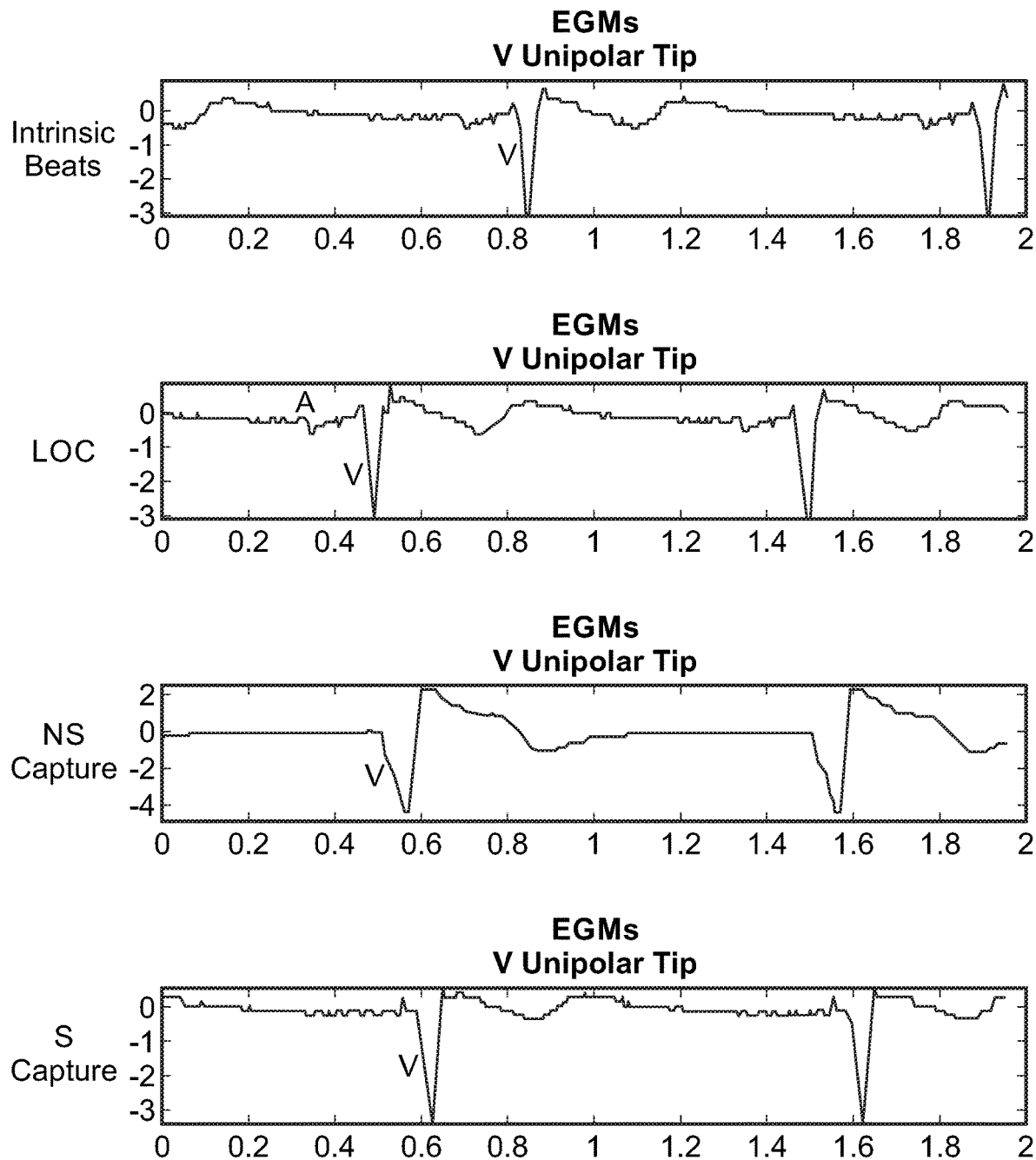
FIG. 3B illustrates examples of cardiac activity signals collected over a HIS sensing channel in connection with HBP achieving different types of HBP capture.

FIG. 3B illustrates examples of cardiac activity signals collected over a HIS sensing channel in connection with HBP achieving different types of HBP capture. The HIS sensing channel utilized a unipolar tip electrode located proximate the HIS bundle. The HIS sensing vector is defined between the tip electrode and the CAN electrode of the IMD. An atrial (A) event marker "A" and a ventricular (V) event "V" is noted on each of the IEGM signals. The cardiac activity signals represent IEGM signals collected over approximately 2 ms. The top panel corresponds to intrinsic heartbeats. The second from top panel corresponds to a beat in which HBP is delivered and achieves nonselective capture. The second from the bottom panel corresponds to a beat in which HBP is delivered but achieves myocardial only capture. The bottom panel corresponds to a beat in which HBP is delivered, but does not achieve any capture, namely loss of capture.

Each of the panels illustrate the ventricular event from the far field. The far field component of each signal is well-defined and very readily apparent. In the intrinsic beat, myocardial only beat and loss of capture beat, the A event and the V event have similar magnitudes. In connection with the nonselective capture beat, the V event induces a larger signal then the A event.

Figure 4:
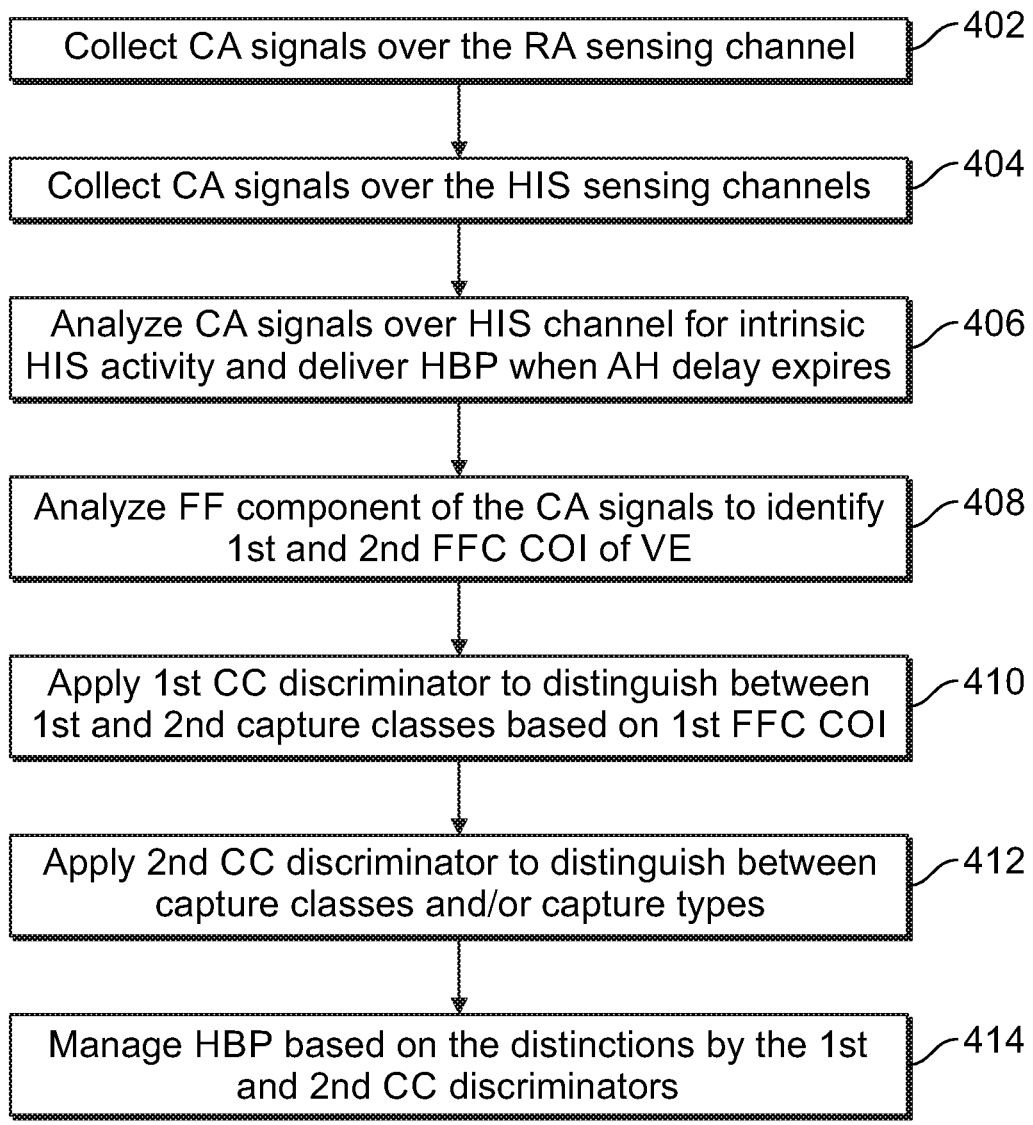
FIG. 4 is a flow chart illustrating a method for identifying capture types in accordance with an embodiment herein.

FIG. 4 is a flow chart illustrating a method for identifying capture types in accordance with an embodiment herein. The process of FIG. 4 utilizes the AV interval to VE onset as a first class discriminator to distinguish between capture classes, and utilizes a VE width of the far field (FF) component as a second class discriminator to distinguish between two further capture classes. Additional or alternative FFC characteristic of interest (COI) may include the VE area and/or VE maximum slope.

At 402, one or more processors begin collecting CA signals over the RA sensing channel. For example, the CA signals are collected along the sensing vector that utilizes one or more RA electrodes on an RA lead. The one or more RA electrodes may be on the same lead or a different lead from the HIS electrodes. The one or more RA electrodes are spaced apart from the HIS electrodes. The RA electrodes may be configured in a bipolar or unipolar sensing configuration. The RA sensing channel may provide CA signals as a wideband signal or a narrowband signal. The RA electrodes may be configured to deliver RA pacing. During each intrinsic or paced atrial event, the one or more processors record the point in time at which intrinsic or paced atrial event occurred. An AH timer is started upon detection of the intrinsic or paced atrial event. The AH timer corresponds to a programmed delay between atrial activity and activity at the HIS bundle.

At 404, the one or more processors collect CA signals over a HIS sensing channel utilizing one or more HIS electrodes that define a HIS sensing vector. It is recognized that the HIS sensing channel and HIS sensing vector differ from the RA sensing channel and RA sensing vector, respectively, and thus exhibit different signal amplitudes and morphologies for components related to atrial events, HIS propagation and ventricular events. For example, an atrial event related component of CA signals sensed over a HIS sensing channel would exhibit a smaller amplitude and/or different overall morphology, as compared to an atrial event related component of CA signals sensed over an RA sensing channel. Similarly, HIS propagation related components of CA signals sensed over a HIS sensing channel exhibit a greater amplitude and/or different morphology as compared to the HIS propagation related component of CA signals sensed over an RA sensing channel. In some instances, the CA signals sensed over the RA sensing channel do not exhibit any component with a distinct morphology related to HIS propagation. As a further example, CA signals sensed over an RA sensing channel exhibit a distinct near field component associated with an atrial event and a separate far field component associated with a ventricular event. In contrast, CA signals sensed over a HIS sensing channel do not exhibit distinct separate components for atrial and ventricular events, and in addition include a HIS propagation related component.

At 406, the one or more processors analyze the CA signals collected over the HIS sensing channel in search of intrinsic conduction before the AH timer times out (e.g. the AH delay expires). When intrinsic conduction is detected over the HIS channel within the programmed AH delay, the one or more processors suspend HBP for the current heartbeat. Alternatively, when intrinsic conduction is not detected over the HIS channel within the programmed AH delay and the AH timer times out, the one or more processors direct the pulse generator to deliver HBP along a HIS pacing vector that includes one or more HIS electrodes.

The operations at 402 to 406 may be implemented for a single beat, based on an ensemble of beats or repeated multiple times in connection with a series of beats. The CA signals collected over the RA sensing channel include an FF component associated with ventricular events.

At 408, the one or more processors analyze the FF component of the CA signals collected over the RA sensing channel to identify first and second FF component (FFC) characteristic of interest (COI) of the ventricular event. Various examples are described herein in connection with how to identify first and second FFC COIs.

At 410, the one or more processors utilize the first FFC COI to apply a first capture class (CC) discriminator to distinguish between first and second capture classes, wherein at least one of the first and second capture classes includes two or more capture types.

At 412, the one or more processors utilize the second FFC COI to apply a second CC discriminator to distinguish between at least one of i) the first and second capture types within the first capture class, or ii) third and fourth capture classes. At 414, the one or more processors manage HIS bundle pacing based on the distinctions by the first and second CC discriminators. For example, the HIS bundle pacing may be managed in accordance with the methods and systems described in the Co-pending Applications.

In accordance with new and unique aspects herein, by utilizing the RA sensing channel, embodiments are able to easily measure an end of a P-wave and start a refractory window during which activity is not utilized to drive pacing decisions. Instead, during a refractory window, embodiments herein measure features of the far field component and, among other things, store a some of the signals below a baseline, first and last points of the FF component, and calculated difference between nonadjacent points for the maximum slope.

Various combinations of FFC characteristics of interest may be utilized in the first and second CC discriminators. Nonlimiting examples of FFC characteristics of interest include the AV interval to VE onset, VE width, VE area and VE maximum slope. Certain FFC COI enable sorting between certain capture classes. For example, the AV interval to VE onset and the VE area may afford good FFC characteristics of interest to sort between one class including selective and nonselective capture and a second class including myocardial only and LOC. Additionally or alternatively, the VE width and VE maximum slope may be utilized to sort myocardial only capture from other types of capture and/or to sort nonselective capture from selective capture and LOC.

By way of example, the first capture class discriminator may also be referred to as a group discriminator as it distinguishes between groups or classes of capture types, and not between individual capture types. For example, the first capture class discriminator may correspond to a first timing threshold that is time to such that an AV interval to VE onset below the first timing threshold are placed in the first group and those above the first timing threshold are placed in the second group. It should be noted that the first timing threshold is not timed to positioned between selective and non-selective capture, but instead to group both selective and nonselective capture in a common class.

At least one of the capture groups or capture classes includes more than one type of capture. For example, the one or more processors may apply a first capture class discriminator to distinguish between a first capture group/class that includes S, NS, and myocardial only, and a second capture group/class that includes both intrinsic and LOC. Various other combinations of capture types are described herein which may be grouped together in a common class based on various FF component COIs.

Figure 5:
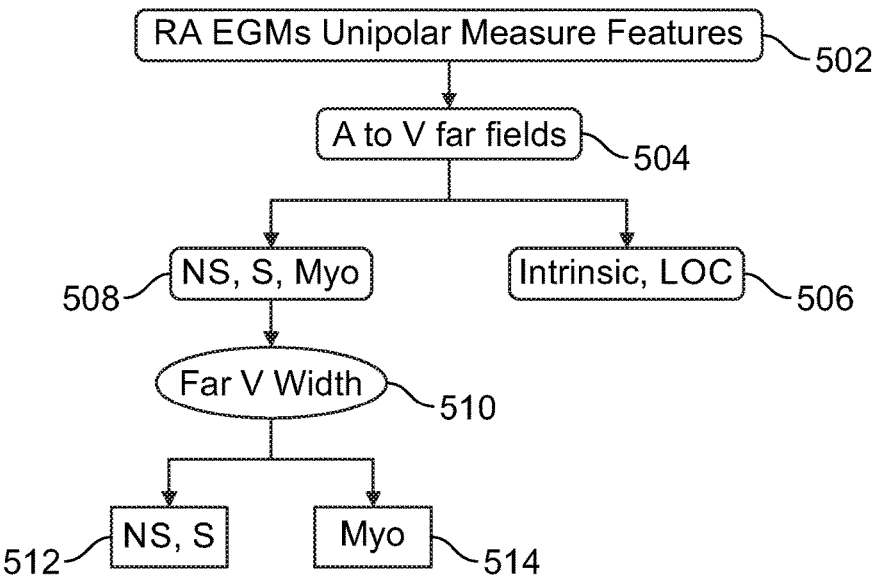
FIG. 5 illustrates a process for distinguishing between capture classes in accordance with embodiments herein.

FIG. 5 illustrates a process for distinguishing between capture classes in accordance with embodiments herein. At 502, the one or more processors collect CA signals over the RA sensing channel utilizing the RA electrode. The CA signals include a far field component associated with a ventricular event.

At 504, the one or more processors analyze the far field component to identify a first FFC characteristic of interest of the ventricular event. In the embodiment of FIG. 5, the FFC COI represents the AV interval between the atrial event and onset of the ventricular event (also referred to as "AV interval to VE onset").

At 506, the one or more processors apply a first CC discriminator to distinguish between first and second capture classes utilizing the first FFC COI (e.g. the A-V interval to VE onset).

Figure 6:
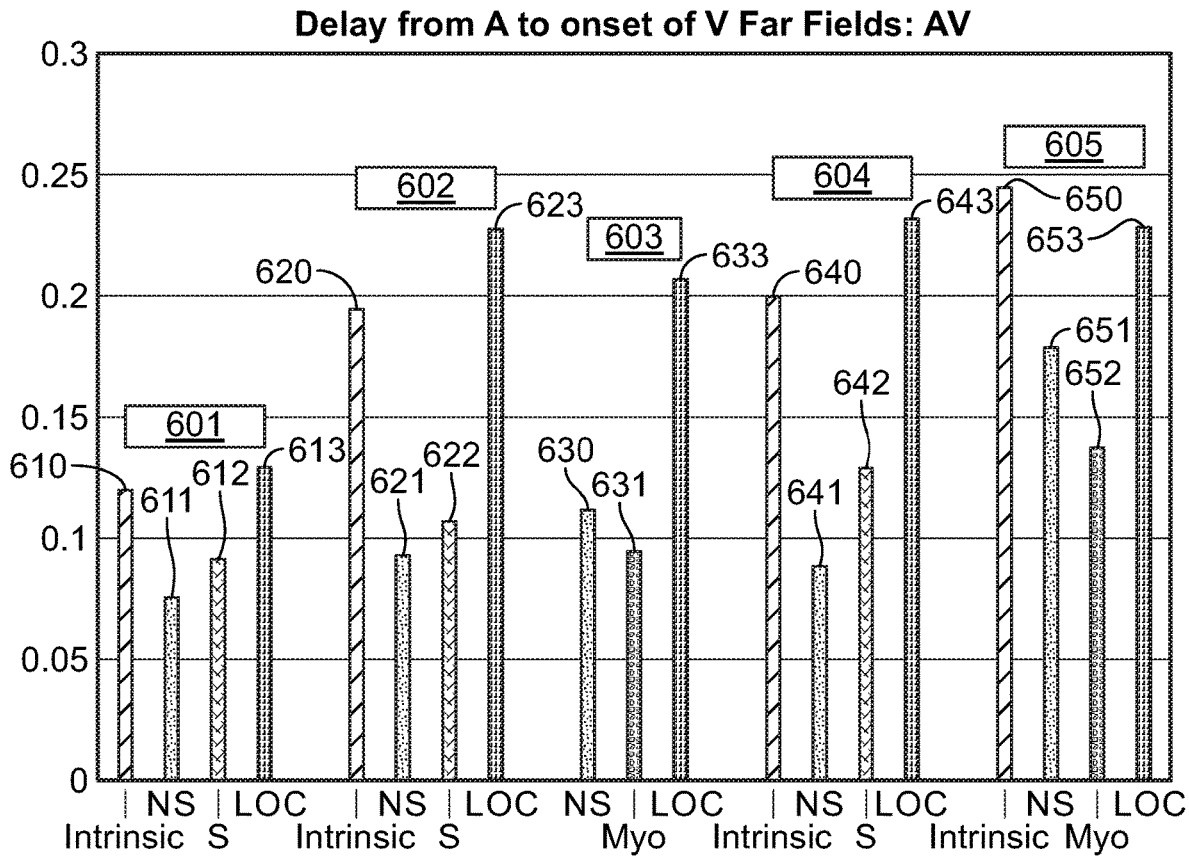
FIG. 6 illustrates examples for AV intervals that may be exhibited by various patients depending upon the type of capture achieved in connection with HBP.

FIG. 6 illustrates examples for AV intervals that may be exhibited by various patients depending upon the type of capture achieved in connection with HBP. In the example of FIG. 6, AV intervals are shown for five potential patients 601-605. For patient 601, AV intervals are shown for an intrinsic beat 610, an HBP beat 611 that achieves nonselective capture, and HBP beat 612 that achieved selective capture and an HBP beat 613 that did not achieve capture (LOC). For patient 602, AV intervals were measured for an intrinsic beat 620, an HBP beat 621 that achieved nonselective capture, an HBP beat 622 that achieved selective capture and an HBP beat 623 that exhibited LOC. For patient 603, AV intervals were measured for an intrinsic beat 630, and HBP beat 631 that achieved myocardium only capture, and an HBP beat 633 that exhibited LOC. For patient 604, AV intervals were measured for an intrinsic beat 640, an HBP beat 641 that achieved nonselective capture, an HBP beat 642 that achieved selective capture and an HBP beat 643 that exhibited LOC. For patient 605, AV intervals were measured for an intrinsic beat 650, an HBP beat 651 that achieved nonselective capture, an HBP beat 652 that achieved myocardium only capture and an HBP beat 653 that exhibited LOC.

The measurements in FIG. 6 indicate that the A-V interval during beats that exhibit nonselective, selective and myocardial only capture are notably shorter than the AV intervals during an intrinsic beat or a beat in which HBP did not achieve capture (LOC). Accordingly, in accordance with embodiments herein, the A-V interval can be used as a far field component characteristic of interest when distinguishing between a first capture class that includes selective, nonselective and myocardial only capture, and a second capture class that includes intrinsic beats and loss of capture beats.

Returning to the process of FIG. 5, at 504, the A-V interval is utilized to distinguish between a first capture class that includes selective, nonselective and myocardial only, and a second capture class that includes intrinsic and LOC beats. When the AV interval measured at 504 is greater than a predetermined threshold, flow moves to 506 and the beat is classified as either intrinsic or LOC. The one or more processors is able to distinguish between an intrinsic beat and LOC based on whether HBP pacing was delivered to the HIS.

Alternatively, at 504, when the A-V interval is less than the predetermined threshold, flow moves to 508. At 508, the one or more processors determine that the beat falls within the first capture class that includes NS, S and myocardial only.

At 510, the one or more processors apply a second CC discriminator to further distinguish between the capture types within the first class. The second CC discriminator utilizes another FF component COI, namely the width of the FF component for the ventricular event (also referred to as the VE width).

Figure 7:
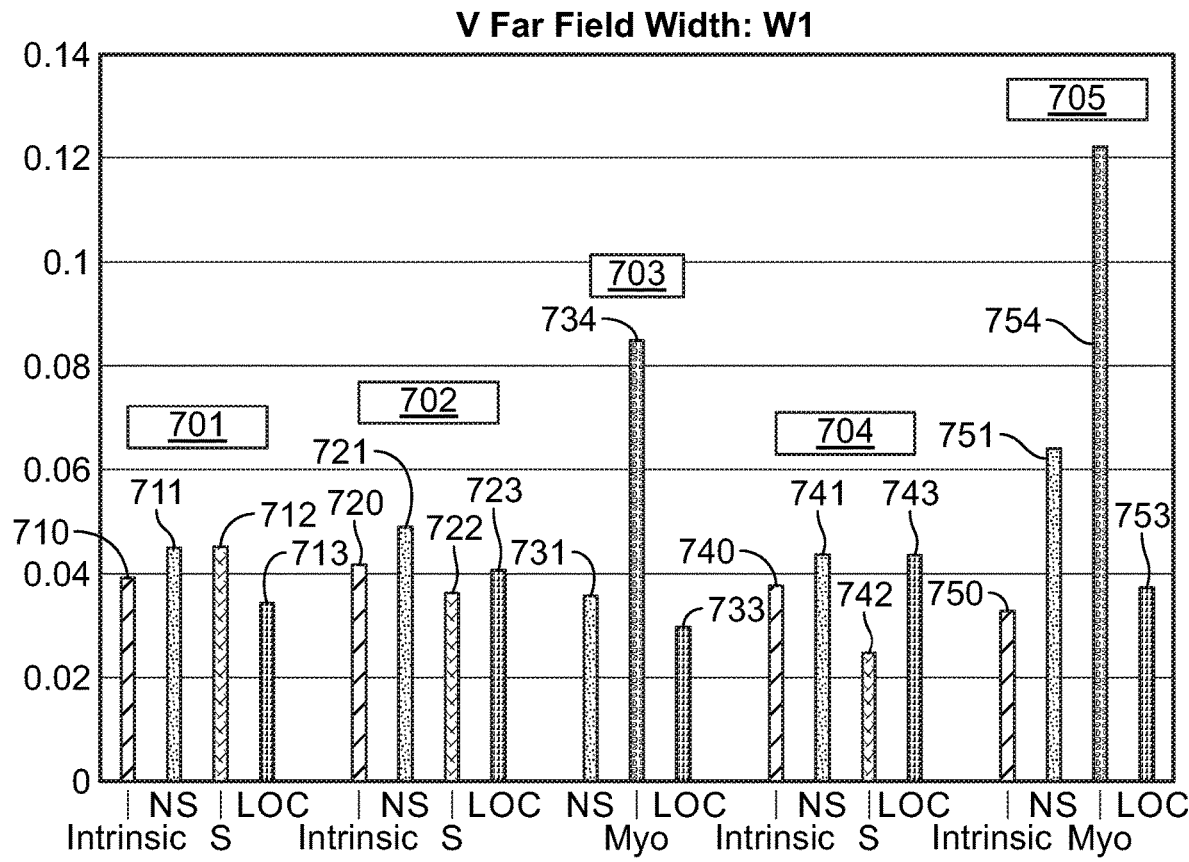
FIG. 7 illustrates examples for the VE widths that may be exhibited by various patients depending upon the type of capture achieved in connection with HBP.

FIG. 7 illustrates examples for the VE widths that may be exhibited by various patients depending upon the type of capture achieved in connection with HBP. In the example of FIG. 7, VE widths are shown for five potential patients 701-705. For patient 701, the VE widths are shown for an intrinsic beat 710, an HBP beat 711 that achieves nonselective capture, and HBP beat 712 that achieved selective capture and an HBP beat 713 that did not achieve capture (LOC). For patient 702, the VE widths were measured for an intrinsic beat 720, an HBP beat 721 that achieved nonselective capture, an HBP beat 722 that achieved selective capture and an HBP beat 723 that exhibited LOC. For patient 703, the VE widths were measured for an HBP beat 731 that achieved nonselective capture, a HBP beat 734 that achieved myocardium only capture, and an HBP beat 733 that exhibited LOC. For patient 704, the VE widths were measured for an intrinsic beat 740, an HBP beat 741 that achieved nonselective capture, an HBP beat 742 that achieved selective capture and an HBP beat 743 that exhibited LOC. For patient 705, the VE widths were measured for an intrinsic beat 750, an HBP beat 751 that achieved nonselective capture, an HBP beat 752 that achieved myocardium only capture and an HBP beat 753 that exhibited LOC.

From the measurements in FIG. 7, it can be seen that the VE width during HBP beats that achieved myocardial only capture are substantially larger than the VE widths during HBP beats that achieve selective, nonselective or loss of capture, as well as an intrinsic beat. Accordingly, in accordance with embodiments herein, the VE widths can be used as a far field component characteristic of interest when distinguishing between the myocardial only capture type, and a third capture class that includes selective and nonselective capture.

Returning to the process of FIG. 5, at 510, the VE width is utilized to distinguish between a first class type (myocardial only) and a third capture class that includes selective and nonselective capture.

When the VE width measured at 510 is greater than a predetermined threshold, flow moves to 514 and the beat is classified as a myocardial only capture type. Alternatively, at 510, when the VE width is less than the predetermined threshold, flow moves to 512. At 512, the one or more processors labels the beat to fall within the third capture class that includes selective and nonselective capture. Optionally, additional analysis may be implemented at 512 to distinguish between selective and nonselective capture as described in embodiments herein and/or as described in the co-pending applications incorporated herein by reference. For example, characteristics of the evoked response may be analyzed as explained in the co-pending applications incorporated herein.

The threshold utilized at 504 and 510 to distinguish between capture classes may be determined in various manners. For example, values for the FFC COIs may be collected over time for a patient population, such as during in clinic studies, during device implantation or thereafter throughout the useful life of an IMD. The FCC COIs may be determined in real time while delivering various HBP energy levels to patients, with the resulting data conveyed to a remote server. Additionally or alternatively, the raw CA signals collected over an RA sensing channel, during HBP, may be collected over time for various patients and transmitted from an IMD to a local external device and subsequently to a remote server. The raw CA signals may be transmitted with device markers identified by the IMD during HBP. For example, when the IMD performs an HBP capture test, the IMD may wirelessly transmit the CA signals from the RA sensing channel along with markers designating the type of capture that was achieved when collecting the CA signals. The remote server may collect the CA signals and device designated capture types for a patient population over time and, in connection there with, measure FFC COIs (e.g. A-V interval to ventricular event onset, area within the CA signal for the ventricular event, VE width) as described herein.

For example, when patients experience a loss of capture, the A-V interval to the onset of the ventricular event is notably longer than the A-V interval to VE onset for patients who experience myocardial only or nonselective capture. As one nonlimiting example, the A-V interval to VE onset may be greater than 200 ms during loss of capture, but less than 150 ms during myocardial only or nonselective capture.

As another example, when patients experience myocardial only capture the VE area and VE width may be substantially larger than the VE area and VE when the same patients experience nonselective capture or loss of capture.

As one nonlimiting example, the VE width during myocardial only capture may be greater than 40 ms, while the VE width during nonselective capture and loss of capture is at or below 30 ms. As a another nonlimiting example, the VE area for patients experiencing myocardial only capture may be greater than 50, while the VE area for patients experiencing nonselective capture may be around 40 and the VE area for patients experiencing loss of capture will be below 20 or near 10. The foregoing numeric examples are merely nonlimiting examples and will vary between patients, patient populations, lead configurations, pacing vectors, patient heart conditions and the like.

Figure 8:
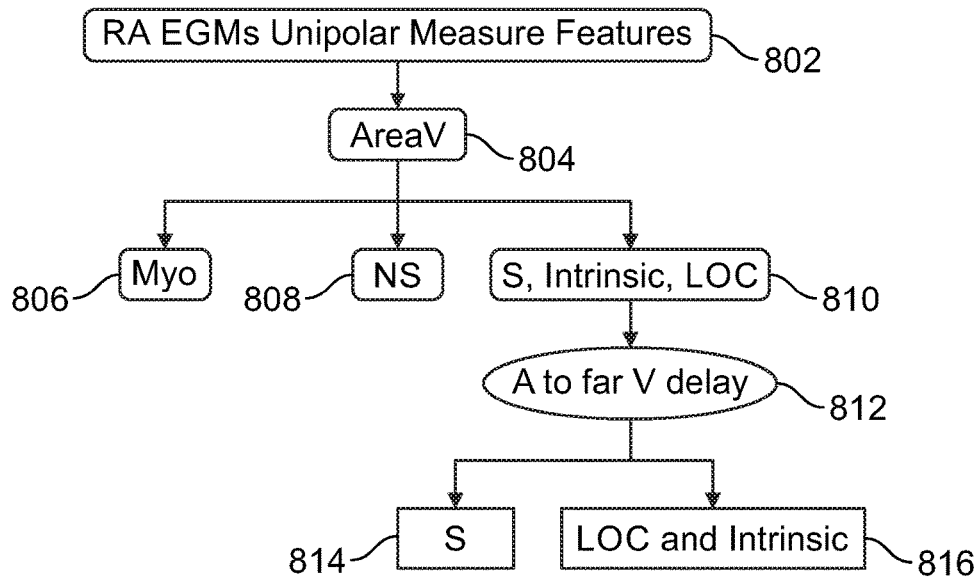
FIG. 8 illustrates a process for distinguishing between capture classes in accordance with an alternative embodiment herein.

FIG. 8 illustrates a process for distinguishing between capture classes in accordance with an alternative embodiment herein. At 802, the one or more processors collect CA signals over the RA sensing channel utilizing the RA electrode. The CA signals include a far field component associated with a ventricular event.

At 804, the one or more processors analyze the far field component to identify a first FFC characteristic of interest of the ventricular event. In the embodiment of FIG. 8, the FFC COI represents an area within the CA signal associated with the ventricular event (also referred to as the VE area or "area under the curve"). At 806, the one or more processors apply a first CC discriminator to distinguish between first and second capture classes utilizing the first FFC COI (e.g. the VE area). The first CC discriminator may apply a combination of thresholds, such as upper and lower thresholds. When the VE area exceeds the upper threshold, the one or more processors may determine that the FFC COI is indicative of myocardial only capture and thus flow moves to 806. When the VE area is between the upper and lower thresholds, flow moves to 808. When the VE area falls below the lower threshold, the one or more processors may determine that the FFC COI is indicative of a first-class that includes selective capture, intrinsic beats and loss of capture, and thus flow moves to 810.

At 806, the one or more processors classify the beat as a myocardial only capture type of beat. At 808, the one or more processors classify the beat as a nonselective capture type of beat. At 810, the one or more processors determined that the beat is within a class including selective capture, and intrinsic beat and loss of capture. Flow moves from 810 to 812.

At 812, the one or more processors apply a second CC discriminator to further distinguish between the capture types within the current class. The second CC discriminator utilizes another FF component COI, namely the A-V interval to VE onset. As noted above in connection with FIG. 6 the A-V interval to VE onset for selective capture is notably shorter than the AV intervals to VE onset during an intrinsic beat or an LOC beat. Accordingly, the A-V interval to VE onset can be used when distinguishing between selective, LOC and intrinsic beats. At 812, when the AV interval to VE onset is greater than a predetermined threshold, flow moves to 816 and the beat is classified as either intrinsic or LOC. The one or more processors is able to distinguish between an intrinsic beat and LOC based on whether HBP pacing was delivered to the HIS. Alternatively, at a 12, when the A-V interval is less than the predetermined threshold, flow moves to 814. At 814, the one or more processors determine that the beat corresponds to selective capture. At 806, 808, 814 and 816, the one or more processors may store a label designating the corresponding classification type which is used elsewhere in connection with managing HBP, among other things, as explained herein.

Figure 9:
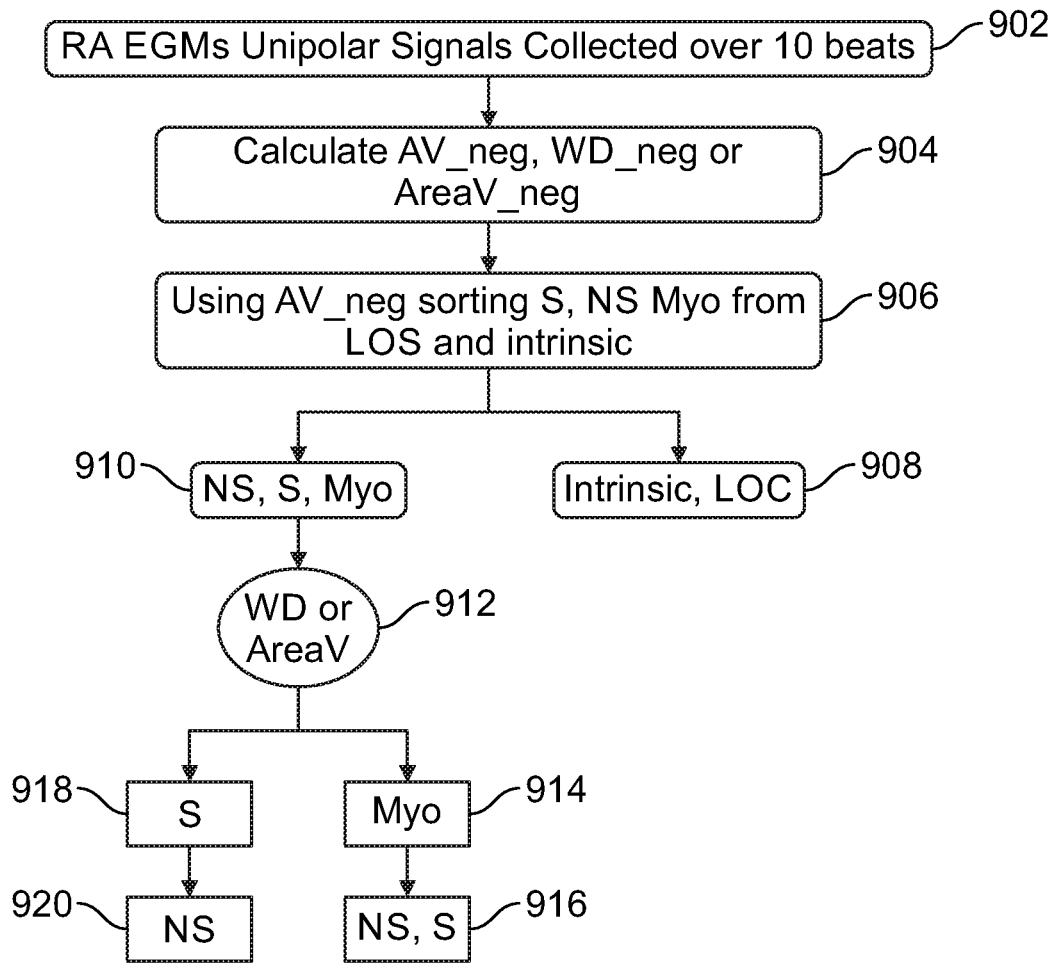
FIG. 9 illustrates a process for distinguishing between capture classes in accordance with an alternative embodiment herein.

FIG. 9 illustrates a process for distinguishing between capture classes in accordance with an alternative embodiment herein. The embodiment of FIG. 9 illustrates a manner in which to differentiate between a first class including selective, nonselective and myocardial only, and a second class including LOC and intrinsic. The embodiment of FIG. 9 further sorts selective and nonselective from myocardial only capture. At 902, the one or more processors collect CA signals over the RA sensing channel utilizing the RA electrode. The CA signals include a far field component associated with a ventricular event. In the example of FIG. 9, the CA signals are collected for a series of beats, such as 10 beats or more. The CA signals for the series of beats may then be combined to form an ensemble of CA signals, such as utilizing averaging or another mathematical function to combine the CA signals. The subsequent operations of FIG. 9 then performed upon the ensemble of CA signals.

At 904, the one or more processors analyze the far field component to calculate first, second and third FFC COIs of the ventricular event. In the embodiment of FIG. 9, the first, second and third FFC COIs represent the A-V interval to VE onset, the VE width and the VE area, respectively.

At 906, the one or more processors apply a first CC discriminator to distinguish between first and second capture classes utilizing the first FFC COI. For example, the first CC discriminator may utilize the A-V interval to VE onset in order to sort between a first capture class, including selective, nonselective and myocardial only, and a second capture class including LOC and intrinsic beats. When the A-V interval to VE onset exceeds a threshold, flow branches to 908. At 908, the one or more processors further distinguish between an intrinsic beat and LOC based on whether HBP was delivered.

Alternatively, at 906, when the A-V interval to VE onset falls below the threshold, flow moves to 910. At 910, the one or more processors determined that the ensemble of beats exhibited one of nonselective, selective and myocardial only capture.

At 912, the one or more processors apply one or both of second and third CC discriminator's, such as based on VE width and/or VE area. When utilizing VE width, a threshold may be applied such that a VE width above the threshold is indicative of myocardial only capture, and thus flow would move to 914. At 914, the one or more processors may classify the ensemble of beats to correspond myocardial only capture. Additionally or alternatively, at 914, the one or more processors may apply additional analysis and at 916 distinguish between myocardial only or a capture class that includes selective and nonselective.

Alternatively, at 912, when the VE width is below the threshold, the one or more processors determined that the ensemble of beats corresponds to one of selective and nonselective capture, and thus flow moves to 918. At 918, the one or more processors may simply label the ensemble of beats corresponding to a class that includes selective and nonselective capture without further distinguishing there between. Alternatively, at 918 and 920, the one or more processors may apply additional analysis to distinguish between selective and nonselective capture. For example, characteristics of the evoked response may be analyzed at 918 and/or 920 to distinguish between selective and nonselective capture, such as the processes described in one or more of the co-pending applications incorporated herein.

In accordance with the foregoing embodiments (and as explained elsewhere herein, new and unique aspects are provided based in part on the use of the RA sensing channel to listen for far field ventricular events. By analyzing the CA signals over the RA sensing channel for the far field components described herein, embodiments afford the advantage of being able to see fusion and other local phenomenon occurring proximate the HIS pacing site. Embodiments herein also simplify the algorithms utilized to analyze morphology given that near field atrial field P-wave's are reliably detected over the RA sensing channel and do not present a risk of oversensing P waves, that would otherwise add the need for additional and/or more complex P-wave detection algorithms.

Algorithms for Detecting Far Field Component Characteristics of Interest—Disclosure 60456

Next, new and unique aspects herein are described that afford robust algorithms for detecting far field component COI from CA signals sensed over an RA sensing channel (e.g. RA IEGMs). While embodiments are described in connection with CA signals sensed over an RA sensing channel that utilizes unipolar RA sensing, additionally or alternatively, the algorithms for detecting FFC COI's may be applied to CA signals sensed entirely or at least partially over a HIS sensing channel (e.g. HIS IEGMs).

Figure 10:
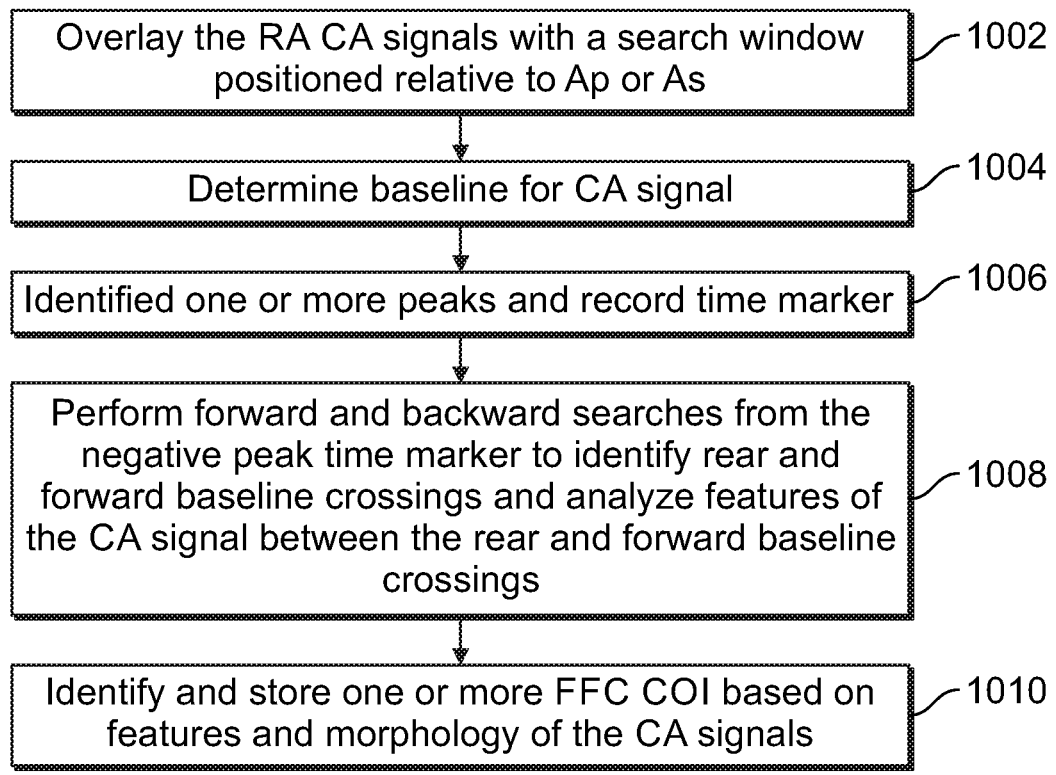
FIG. 10 illustrates a method for analyzing FF components of CA signals collected over an RA sensing channel to identify far-field component (FFC) characteristic of interest (COI) for a ventricular event.

FIG. 10 illustrates a method for analyzing FF components of CA signals collected over an RA sensing channel to identify FFC COI for a ventricular event.

At 1002, the one or more processors overlay a search window on the CA signals collected over the RA sensing channel. The search window is positioned to follow the paced or sensed atrial event by a predetermined amount of time. The predetermined amount of time may be programmed to be a function of the AH delay and a delta. The AH delay represents a programmed delay between an intrinsic or paced atrial event and a point in time when an IMD is programmed to pace the HIS bundle, if no intrinsic event is detected earlier at the HIS bundle. For example, the search window may be positioned to begin at a point along the CA signals corresponding to the AH delay~X milliseconds. The search window would then have a duration to extend over a period of time during which a ventricular event is expected to occur, even when it is assumed that the patient has a wide QRS complex (e.g. in connection with patients experiencing bundle branch block).

Figure 11:
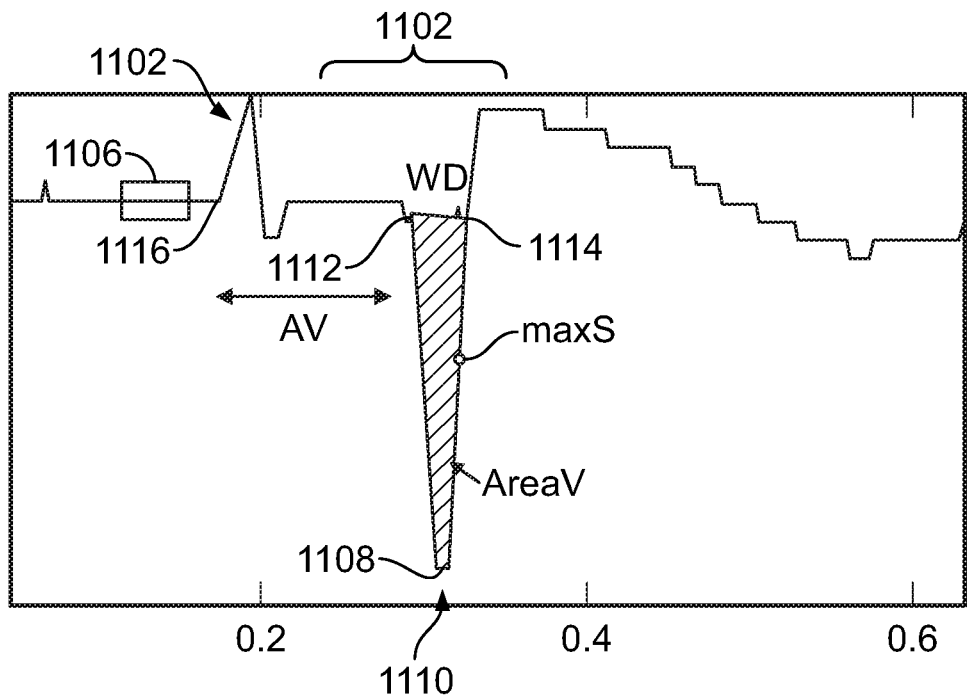
FIG. 11 illustrates an example of a CA signal (an IEGM signal) collected over an RA sensing channel, during one beat, that is analyzed in connection with embodiments herein

FIG. 11 illustrates an example of a CA signal (an IEGM signal) collected over an RA sensing channel, during one beat, that is analyzed in connection with the operations of FIG. 10. The CA signal begins with an atrial event 1102. The operation at 1102 sets a search window, such as the window 1104 that is spaced a predetermined time after the peak and/or onset of the atrial event 1102.

Returning to FIG. 10, at 1004, the one or more processors determine a baseline value in the CA signal. The baseline value may represent a level of the CA signal a few milliseconds before the atrial event and/or before the ventricular event. Additionally or alternatively, the baseline value may be derived from an ensemble average or other mathematical combination of CA signals for multiple beats, where the baseline represents the ensemble average of the CA signal shortly before the onset of the atrial event or shortly before onset of the ventricular event. In the example of FIG. 11, the baseline may correspond to the level in region 1106 preceding onset of the atrial event.

At 1006, the one or more processors identify a peak of the CA signal within the search window and record a time marker corresponding to the peak. The peak may be positive or negative. Alternatively, the one or more processors may determine both a maximum positive peak and a maximum negative peak of the CA signals. In the example of FIG. 11, a negative peak 1108 is identified and a negative peak time marker is recorded in connection with the time 1110.

At 1008, the one or more processors conduct separate forward and backward searches along the CA signals from the negative peak time marker 1110 to identify the onset intercept (X) and termination intercept (Y) points in time at which the CA signal intercepts an intercept level. The intercept level may correspond to the baseline (determined at 1004) or may correspond to a level defined by the baseline plus/minus a preprogrammed delta (e.g. baseline -/+XmV). In the example of FIG. 11, the X and Y intercepts correspond to the points in time noted at 1112 and 1114, respectively. The intercept point 1112 is also referred to as the ventricular event onset (VE onset) or onset of the ventricular event (onset of VE), while the intercept point 1114 is also referred to as VE termination or termination of VE. In the example of FIG. 11, the X and Y intercept points 1112 and 1114 correspond to the point in time in which the CA signal crosses a voltage level below the baseline 1106 minus XmV.

During the separate forward and backward searches, the one or more processors separately analyze points along the CA signal in both directions. The determination of the onset intercept X is rendered independent of the determination of the termination intercept Y.

Additionally or alternatively, the analysis may include summing values along the CA signal (e.g. in connection with calculating the area) and calculating derivatives at various points along the CA signal (e.g. dV/dt, wherein V represents the instantaneous value of the CA signal at a point in time (t)).

In accordance with new and unique aspects herein, embodiments avoid detecting noise at onset of a ventricular event, first identifying largest peak and valley in the search window and resetting the crossings (also referred to as intercept points) separately for the forward and backward searches from the largest peak and separately for the forward and backward searches from the largest valley. In accordance with new and unique aspects herein, embodiments avoid summation over the wrong region, by resetting the baseline crossings (also referred to as intercept points) separately for the forward and backward searches.

At 1010, the one or more processors identify various FFC COI. For example, the one or more processors may identify, as an FFC COI, an AV interval between onset of the atrial event and onset of the ventricular event. In the example of FIG. 11, the AV interval to the VE onset is denoted as AV extending between the onset 1116 of the atrial event and the onset 1112 of the ventricular event. Additionally or alternatively, the FFC COI may represent the AV interval between the peak of the atrial event and onset (1112) of the ventricular event.

As another example, the FFC COI may represent the ventricular event (VE) width which corresponds to the time interval between the X and Y baseline crossings 1112 and 1114. In the example of FIG. 11, the VE width is denoted at WD between the baseline crossings 1112 to 1114 (also corresponding to VE onset and termination).

As another example, the FFC COI may represent the VE area and/or the maximum slope/derivative exhibited in the CA signal during the VE. In the example of FIG. 11, the VE area is denoted as AreaV (corresponding to the shaded area within the ventricular event), while the maximum slope is denoted as maxS (corresponding to a point along the trailing edge of the ventricular event).

The FFC COI are stored for subsequent use as described in accordance with the various embodiments herein, among other things, for implementing capture class discrimination.

The process of FIG. 10 affords a simple and robust manner of identifying features and characteristics of interest from far field components. Among other things, the process utilizes the peak of the ventricular event as an "anchor" from which forward and reverse searches are conducted to identify starting and points of onset and termination for the ventricular event. By utilizing the peak of the ventricular event, embodiments herein avoid issues experienced by other types of forward searches, that have no knowledge of the VE peak. For example, conventional forward searches may prematurely terminate due to noise or incorrectly calculate the integration of the area of the VE, such as due to an unduly high threshold/baseline.

While the foregoing example of FIG. 11 is described in connection with an RA IEGM unipolar signal that exhibits a negative peak during the ventricular event, it is recognized that the same process may be applied in connection with positive peaks or with other sensing vectors/sensing channels.

While the process of FIG. 10 is described in connection with identifying FFC COI for HBP capture determination, the process of FIG. 10 may be implemented in connection with other aspects of IMDs. For example, the process of FIG. 10 may be utilized to identify COI in connection with an evoked response in a pacemaker.

Figure 12:
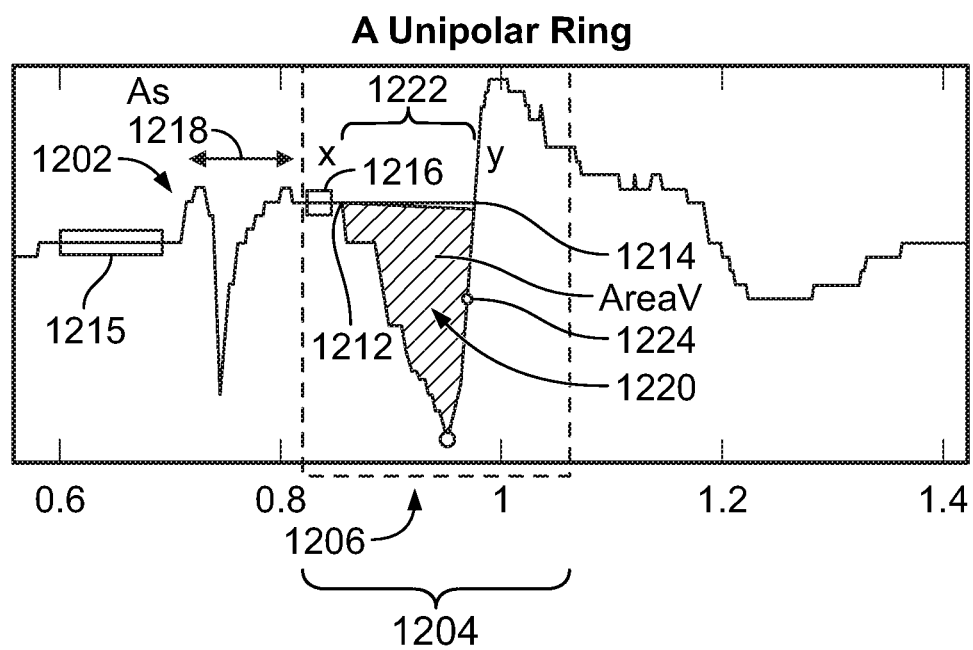
FIG. 12 illustrates another example of the CA signal that is analyzed in accordance with embodiments herein

FIG. 12 illustrates another example of the CA signal, collected over an RA sensing channel, that is analyzed in accordance with the process of FIG. 10 and other processes described herein. In FIG. 12, an intrinsic atrial event 1202 is sensed, followed by the designation of a sensing window 1204 set to begin a predetermined time after either onset or the peak of the intrinsic atrial event. Within the search window, the peak of the ventricular event is identified at 1206. Thereafter, forward and backward searches are initiated to identify the onset intercept 1212 and termination intercept 1214 of the ventricular event. In the example of FIG. 12, the RA sensing channel utilizes a wideband signal which has the potential to drift over the course of a beat. For example, the baseline may have one level preceding an atrial sensed event, such as in region 1215, and the baseline may have a different level preceding the ventricular event, such as in region 1216. To account for baseline drift, embodiments herein, derive a level for the baseline from the level of the CA signal from a few samples preceding the ventricular event, such as the CA signal samples in the baseline search segment 1216. The features of the CA signal are analyzed to identify the AV interval to VE onset 1218, the area of the VE event 1220, the width 1222 of the VE event and the maximum slope 1224 of the VE event.

Figure 13:
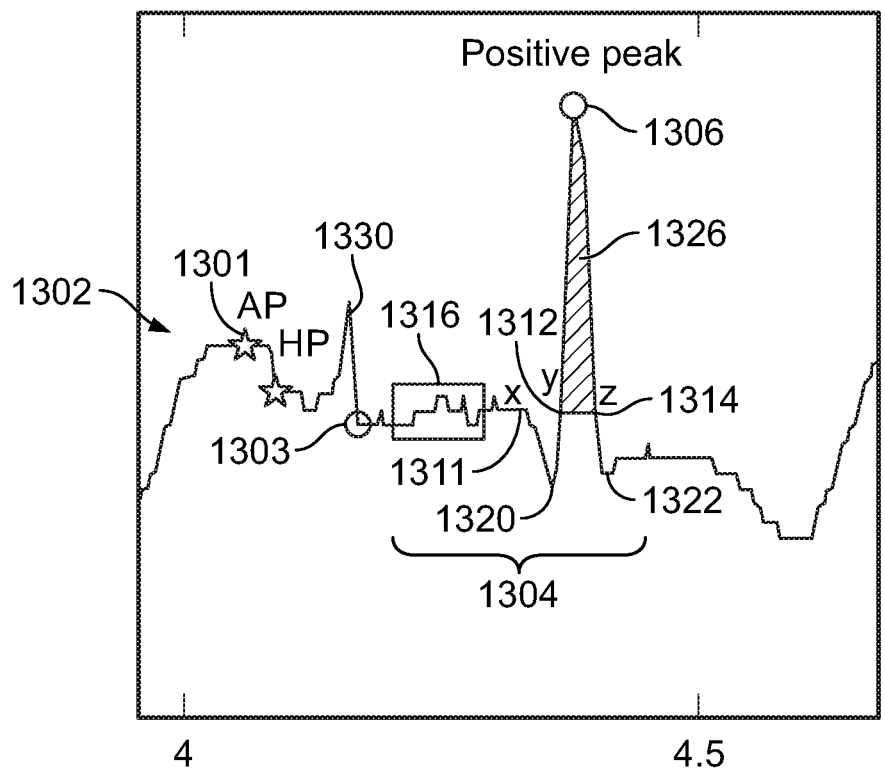
FIG. 13 illustrates another example of a CA signal that is analyzed in accordance with embodiments herein

FIG. 13 illustrates another example of a CA signal that is analyzed in accordance with the process of FIG. 10 and other processes described herein. In FIG. 13, the CA signal 1302 is generated in response to a paced atrial event AP at 1301, followed by a HIS paced event at the "star" labeled HP. The one or more processors designate a sensing window 1304 set to begin a predetermined time after the paced atrial event AP at 1301. Within the search window 1304, the peak of the ventricular event is identified at 1306. The baseline is derived from an average level of the CA signal preceding the ventricular event, over a baseline search segment 1316. Forward and backward searches are initiated to identify the onset 1312 and termination 1314 of the peak 1306 of the ventricular event 1318. In the example of FIG. 13, the VE event includes a positive peak at 1306 that is preceded by a shallow negative peak 1320 and followed by a shallow second negative peak 1322. The negative peaks 1320 and 1322 are substantially smaller than the positive peak 1306.

In accordance with the embodiment of FIG. 13, the process identifies, as the FFC COI, the VE width as the width between onset 1312 and termination 1314 of the positive region, the VE area as the area 1326 of the positive region. In the example of FIG. 13, embodiments herein avoid analyzing the signal at 1330 as a false ventricular event.

As another FFC COI, the process may identify the AV interval from the atrial paced event AP to various features of the ventricular event. For example, the end point of the AV interval may correspond to the endpoint/termination of the QRS complex, which corresponds to the final crossing 1314 of the positive region. Optionally, the AV interval may be from the AP to onset of the QRS complex at onset 1311 of the first negative region. Optionally, the AV interval may be from the AP to onset 1312 of the first positive region. Optionally, the AV interval may be from the AP to the peak 1306 of the first positive region.

As another FFC COI, the process may identify the HV interval from the HIS paced event HP to various features of the ventricular event. For example, the end point of the HV interval may correspond to the endpoint/termination of the QRS complex, which corresponds to the final crossing 1314 of the positive region. Optionally, the HV interval may be from the AP to onset of the QRS complex at onset 1311 of the first negative region. Optionally, the HV interval may be from the HP to onset 1312 of the first positive region. Optionally, the HV interval may be from the HP to the peak 1306 of the first positive region.

Figure 14:
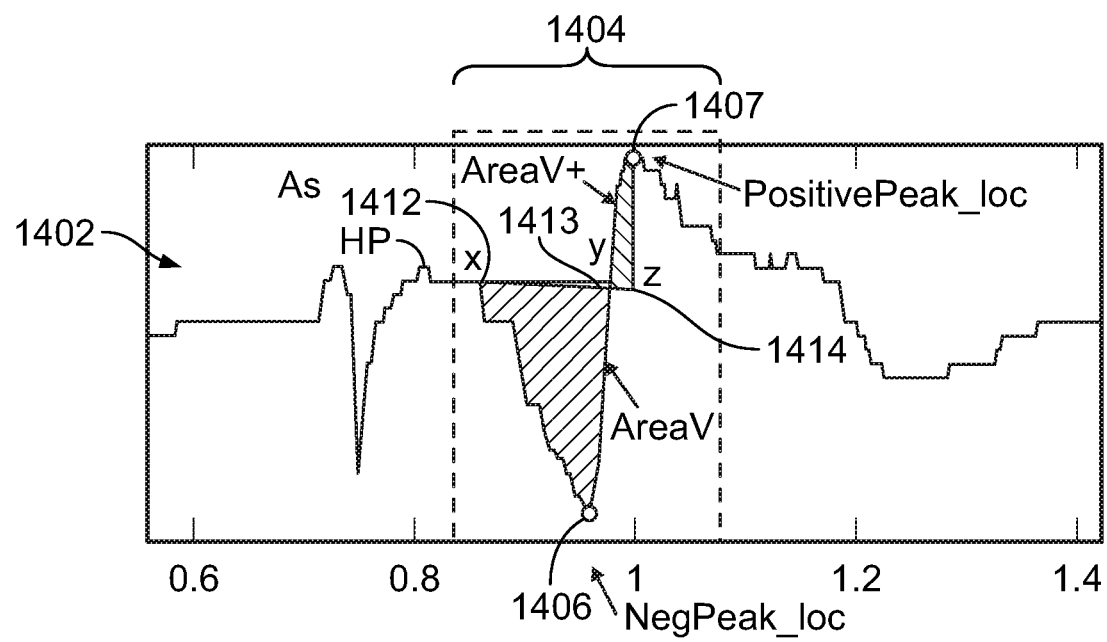
FIG. 14 illustrates another example of a CA signal that is analyzed in accordance with embodiments herein

FIG. 14 illustrates another example of a CA signal that is analyzed in accordance with the process of FIG. 10 or other processes described herein. In FIG. 14, the CA signal 1402 includes an intrinsic atrial event that begins at marker AS followed by a HIS paced event at HP. The one or more processors designate a sensing window 1404 set to begin a predetermined time after the intrinsic atrial event AS. Within the search window 1404, the ventricular event exhibits a negative peak 1406 and a positive peak 1407. A baseline is derived from an average the level of the CA signal preceding the ventricular event. Forward and backward searches are separately performed to identify the onset 1412 and termination 1414 of the QRS complex, The CA signal 1402 includes negative and positive peaks 1406 and 1407. The one or more processors separately perform backward and forward searches from the negative peak 1406 and identify crossing/intercept points 1412 and 1413 where the CA signal crosses the intercept defined by the baseline −/+a delta. The intercept point 1413 represents an intermediate intercept crossing of the overall QRS complex, a termination intercept of the negative peak 1406 and an onset intercept of the positive peak 1407. The process of FIG. 10 may determine FCC COI by analyzing the positive and negative regions of the VE for QRS width (between negative onset 1412 and positive termination 1414). The one or more processors may determine, as another FFC COI, the negative VE area of the region between onset and termination intercepts 1412, 1413 of the negative region, and/or the positive VE area of the region between onset and termination intercepts 1413, 1414 of the positive region and the like.

It is noted in FIG. 14, that the termination intercept 1414 of the positive region does not drop to the baseline +/−delta. Instead, the one or more processors designate the termination intercept 1414 to occur when the CA signal reaches a maximum positive amplitude within the sensing window 1404.

Additionally or alternatively, the process may determine the FFC COI by analyzing the AV interval from the A event to onset of the VE, the HV interval from the HP event to onset of the VE, the AV interval from the A event to the end of the QRS complex (e.g., As to 1407), the HV interval from the HP event to the end of the QRS complex and the like. Additionally or alternatively, the FFC COI may represent the VE width (e.g., 1412 to 1413) and/or the maximum slope in the CA signal segment between 1406 and 1407. Additionally or alternatively, the process may determine an FFC COI to be the VE area of the negative region (between 1412 and 1413), the VE area of the positive region (between 1413 and 1414), and/or the sum of the VE areas in the positive and negative regions (between 1412 and 1414).

Figure 15:
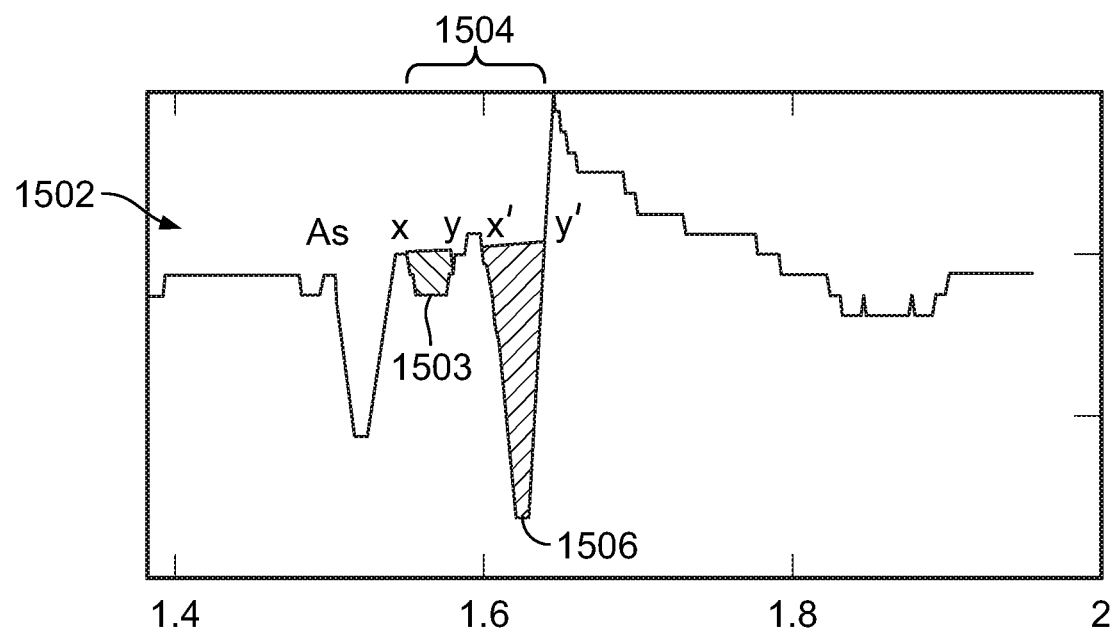
FIG. 15 illustrates another example of a CA signal that is analyzed in accordance with embodiments herein.

FIG. 15 illustrates another example of a CA signal that is analyzed in accordance with the process of FIG. 10 or other processes described herein. In FIG. 15, the CA signal 1502 includes an intrinsic atrial event that begins at marker AS followed by a small negative peak at 1503 and a large negative peak 1506. The one or more processors designate a sensing window 1504 set to begin a predetermined time after the intrinsic atrial event AS. Within the search window 1504, the CA signal exhibits the small negative peak at 1503 and the large negative peak 1506. The process avoids designating the small negative peak 1503 as the ventricular event by continuing to search along the search window 1504 for a larger peak. The peak 1506 is identified as the largest peak in the search window 1504 and utilized as the reference point, from which forward and backward searches are separately performed to identify the onset 1512 and termination 1514 of the negative region.

In accordance with new and unique aspects herein, the process avoids incorrectly identifying the peak at 1503 and the related intercept points X and Y, by first searching the window 1504 for a largest peak and then performing forward and backward searches (from the largest peak) for intercepts. By doing so, the process identifies peak 1506 and subsequently identifies the intercepts X' and Y' in a simple and robust manner.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing.

More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

All references, including publications, patent applications and patents, cited herein are hereby incorporated by reference to the same extent as if each reference were individually and specifically indicated to be incorporated by reference and were set forth in its entirety herein.

What is claimed is:

1. A system comprising:
    a HIS electrode configured to be located proximate to a HIS bundle;
    a pulse generator coupled to the HIS electrode and configured to deliver HIS bundle pacing (HBP);
    a right atrial (RA) electrode configured to be located in a right atrium;
    sensing circuitry coupled to the RA electrode and configured to define an RA sensing channel that does not utilize the HIS electrode;
    a memory including program instructions;
    a processor, when executing the program instructions, configured to:
        collect cardiac activity (CA) signals over the RA sensing channel utilizing the RA electrode, the CA signals including a far field (FF) component associated with a ventricular event (VE);
        analyze the FF component to identify first and second FF component (FFC) characteristics of interest (COI) of the ventricular event;
        to apply a first capture class (CC) discriminator to distinguish between first and second capture classes based on the first FFC COI,
            wherein the first capture class includes first and second capture types corresponding to two out of i) myocardial-only capture, ii) nonselective capture, iii) selective capture, or iv) intrinsic capture, and
            wherein the second capture class includes a third capture type out of the i) myocardial-only capture, ii) nonselective capture, iii) selective capture, or iv) intrinsic capture;
        apply a second CC discriminator to distinguish between at least one of i) the first and second capture types within the first capture class based on the second FFC COI; and
        manage the HBP based on distinctions by the first and second CC discriminators.

2. The system of claim 1, wherein the first FFC COI corresponds to onset of the VE and wherein the processor is further configured to: determine an activation time between a time of a paced or intrinsic atrial event and the onset of the VE and utilize the activation time to apply the first CC discriminator to distinguish between the first and second capture classes.

3. The system of claim 1, wherein the first FFC COI corresponds to at least one of an atria-ventricular (AV) interval to VE onset, an area of the VE, a width of the VE or a maximum slope of the VE which is utilized as the first FFC COI to apply the first CC discriminator to distinguish between the first and second capture classes.

4. The system of claim 1, wherein the processor is configured:
    to identify the first capture class based on the first CC discriminator;
    to identify the first capture type, within the first capture class, based on the second CC discriminator; and
    manage the HBP based on the identification of the first capture type within the first capture class.

5. The system of claim 1, wherein the first FFC COI corresponds to an atria-ventricular (AV) interval to VE onset and the first CC discriminator distinguishes between a first CC that includes the nonselective, selective and myocardial-only capture and a second CC that includes the intrinsic capture and loss of capture.

6. The system of claim 5, wherein the second FFC COI corresponds to a width of the VE and the second CC discriminator distinguishes between the myocardial-only capture and a third capture class that includes the nonselective and selective capture.

7. The system of claim 5, wherein the second FFC COI corresponds to at least one of an area of the VE or a width of the VE and the second CC discriminator distinguishes between the third and fourth capture classes, the third capture class including the selective and nonselective capture, the fourth capture class including at least the only capture.

8. The system of claim 1, wherein the first FFC COI corresponds to an area of the VE and the first CC discriminator distinguishes between the i) myocardial-only capture, ii) nonselective capture, and iii) the first capture class that includes the selective capture, intrinsic capture and loss of capture.

9. The system of claim 8, wherein the second FFC COI corresponds to an atria-ventricular (AV) interval to VE onset and the second CC discriminator distinguishes between i) the selective capture and a third capture class that includes the loss of capture and intrinsic capture.

10. The system of claim 1, wherein the processor is configured to overlay a search window on the CA signals collected over the RA sensing channel, the search window positioned to follow a paced or sensed atrial event by a predetermined amount of time to align the search window with a period of time during which the VE is expected to occur.

11. The system of claim 1, wherein the processor is further configured to identify a peak in the CA signals and to separately perform forward and backward searches along the CA signals from the peak to identify an onset intercept and a termination intercept of the VE, wherein at least one of the first and second FFC COI is based in part on at least one of the onset and termination intercepts.

12. The system of claim 11, wherein the processor is further configured to identify a largest peak and a largest valley in a search window and to reset intercept points separately for the forward and backward searches from the largest peak and separately for the forward and backward searches from the largest valley.

13. A computer implemented method comprising:
utilizing a processor configured to execute program instructions to perform,
delivering HIS bundle pacing (HBP);
collecting cardiac activity (CA) signals over a right atrial (RA) sensing channel utilizing an RA electrode, the CA signals including a far field (FF) component associated with a ventricular event (VE);
analyzing the FF component to identify first and second FF component (FFC) characteristics of interest (COI) of the ventricular event;
first distinguishing between first and second capture classes (CCs) based on the first FFC COI,
wherein the first capture class includes first and second capture types corresponding to two out of i) myocardial-only capture, ii) nonselective capture, iii) selective capture, or iv) intrinsic capture, and
wherein the second capture class includes a third capture type out of the i) myocardial-only capture, ii) nonselective capture, iii) selective capture, or iv) intrinsic capture;
second distinguishing between the first and second capture types within the first capture class based on the second FFC COI; and
managing the HBP based on the first and second distinguishing operations.

14. The method of claim 13, wherein the first FFC COI corresponds to onset of the VE and wherein the method further comprises determining an activation time between a time of a paced or intrinsic atrial event and onset of the VE and utilize the activation time to apply a first CC discriminator to distinguish between the first and second capture classes.

15. The method of claim 13, wherein the first FFC COI corresponds to at least one of an atria-ventricular (AV) interval to VE onset, an area of the VE, a width of the VE or a maximum slope of the VE which is utilized as the first FFC COI to apply a first CC discriminator to distinguish between the first and second capture classes.

16. The method of claim 13, wherein the first distinguishing between the first and second capture classes is independent of whether fusion occurs between first and second wavefronts proximate a HIS electrode, the first wavefront propagating in response to a paced event at the HIS electrode, the second wavefront corresponding to intrinsic conduction.

17. The method of claim 13, further comprising, during collection of the CA signals over the RA sensing channel, avoiding sensing fusion beats representing a collision between i) a HBP causing the nonselective capture or myocardial-only capture and ii) conduction exiting Purkinje fibers.

18. The method of claim 13, wherein the first FFC COI corresponds to an atria-ventricular (AV) interval to VE onset and the first distinguishing distinguishes between a first CC that includes the nonselective, selective and myocardial-only capture and a second CC that includes the intrinsic capture and loss of capture.

19. The method of claim 18, wherein the second FFC COI corresponds to a width of the VE and the second distinguishing distinguishes between the myocardial-only capture and a third capture class that includes the nonselective and selective capture.

20. The method of claim 13, wherein the second FFC COI corresponds to at least one of an area of the VE or a width of the VE and the second distinguishing distinguishes between third and fourth capture classes, the third capture class including the selective and nonselective capture, the fourth capture class including at least the myocardial-only capture.

21. The method of claim 13, wherein the first FFC COI corresponds to an area of the VE and the first FFC COI distinguishes between i) the myocardial-only capture, ii) the nonselective capture, and iii) a third capture class that includes the selective capture, intrinsic capture and loss of capture.

22. The method of claim 21, wherein the second FFC COI corresponds to an atria-ventricular (AV) interval to VE onset and the second distinguishing distinguishes between i) the selective capture and a third capture class that includes the loss of capture and intrinsic capture.

* * * * *